United States Patent [19]
Prutchi et al.

[11] Patent Number: 5,718,720
[45] Date of Patent: Feb. 17, 1998

[54] IMPLANTABLE CARDIAC STIMULATOR WITH CAPTURE DETECTION AND IMPEDANCE BASED AUTOTUNING OF CAPTURE DETECTION

[75] Inventors: David Prutchi; Patrick J. Paul, both of Lake Jackson, Tex.

[73] Assignee: Sulzer Intermedics Inc., Angleton, Tex.

[21] Appl. No.: 766,526

[22] Filed: Dec. 13, 1996

[51] Int. Cl.⁶ ........................................ A61N 1/37
[52] U.S. Cl. ............................................. 607/28
[58] Field of Search ..................... 607/28, 9, 27, 607/11

[56] References Cited

U.S. PATENT DOCUMENTS

| | | |
|---|---|---|
| 4,140,132 | 2/1979 | Dahl . |
| 4,373,531 | 2/1983 | Wittkampf et al. . |
| 4,537,201 | 8/1985 | Delle-Vedove et al. . |
| 4,686,987 | 8/1987 | Salo et al. . |
| 4,688,573 | 8/1987 | Alt . |
| 4,858,610 | 8/1989 | Callaghan et al. . |
| 4,901,725 | 2/1990 | Nappholz et al. . |
| 4,913,145 | 4/1990 | Stotts . |
| 4,979,507 | 12/1997 | Heinz et al. . |
| 5,154,171 | 10/1992 | Chirife . |
| 5,201,808 | 4/1993 | Steinhaus et al. . |
| 5,413,592 | 5/1995 | Schroeppel .................. 607/18 |
| 5,443,485 | 8/1995 | Housworth et al. .............. 607/28 |
| 5,476,487 | 12/1995 | Sholder ...................... 607/28 |
| 5,507,785 | 4/1996 | Deno ......................... 607/24 |
| 5,531,772 | 7/1996 | Prutchi ...................... 607/17 |

OTHER PUBLICATIONS

Schaldach "Bioelectric Phenomena in Cardiac Pacing", IEEE, Ninth Annual Conference of the Engineering in Medicine and Biology Society 1987.

E, Alt et al., "Feasibility of Using Intracardiac Impedance Measurements for Capture Detection", PACE, vol. 15, Part II, Nov. 1992, pp. 1873–1879.

*Primary Examiner*—Scott M. Getzow
*Attorney, Agent, or Firm*—John R. Merkling

[57] ABSTRACT

An implantable cardiac stimulator for detecting capture or adjusting the strength or duration of pacing pulses by using an evoked response detector and periodically tuning the evoked response detector. When the electric evoked response detector is to be tuned, capture is verified by detecting the mechanical evoked response. As the magnitude of the stimulating pulse is adjusted to isolate the threshold as detected by the mechanical response detector. At the same time, the electrical evoked response is also monitored. The difference between the detected electrical signal following capture as detected by the mechanical response detector and the signal following non-capture is used to tune the electrical evoked response detection apparatus and algorithm. The energy of the pacing pulse can then be optimized by adjusting both strength and duration. A very small safety margin is needed since capture is continuously monitored by the electrical evoked response apparatus and a safety pulse is immediately applied if capture is lost. The safety pulse can be applied in the same cardiac cycle so that the heart beat remains controlled.

24 Claims, 11 Drawing Sheets

IMPLANTABLE CARDIAC STIMULATOR WITH CAPTURE DETECTION AND IMPEDANCE BASED AUTOTUNING OF CAPTURE DETECTION

FIELD OF OUR INVENTION

Our invention relates to rate responsive cardiac pacemakers, and more particularly to cardiac pacemakers which automatically adjust the amplitude of pacing stimulus pulses to conserve energy.

BACKGROUND OF OUR INVENTION

Implanted cardiac pacemakers are employed to assist patients suffering from severe bradycardia or chronotropic incompetence. A cardiac pacemaker "captures" the heart by delivering an electrical pulse to the myocardium of either the atrium or the ventricle during an interval in the cardiac cycle when the cardiac tissue is excitable. The electrical pulse causes depolarization of cardiac cells and contraction of the chamber if the energy of the pacing pulse exceeds a threshold value. It is important that the pulse reliably stimulate contraction or "capture" the heart. At the same time, it is desirable to use as little energy as possible, to extend the useful life of the pacemaker.

The threshold for capture, however, varies in a patient over time. It is therefore desirable to periodically adjust the pulse magnitude and duration to optimize use of pulse energy. Adjustment can be effected manually through the use of an external programmer. An operator verifies capture by visually assessing a detected ECG waveform. It is desirable, however, to provide a pacemaker with means that allow it to automatically determine threshold levels, either in response to a command from the external programmer or as part of the pacemaker's internal procedures and treatment.

For such a procedure to be safe and effective, however, it is important for the pacemaker to be able to verify that capture has taken place, that is, that the heart has been stimulated by a particular pulse. Capture verification has been generally accomplished by detecting and evaluating the electrical evoked response of the heart resulting from stimulation. If capture has not occurred, there will be no evoked potential to detect. Theoretically, each time a stimulating pulse is delivered to the heart, the heart could be monitored to detect the presence or absence of the evoked response. In practice, however, reliable detection of the evoked response is not a simple matter, especially if the evoked response is to be detected with the same electrode used for stimulating the heart. The evoked potential is small in amplitude relative to the residual polarization charge on the electrode resulting from the depolarization pulse. As will be explained below, accurate tuning of the detection circuit is important to assure detection of the evoked electrical response.

Several patents have dealt with techniques to differentiate the evoked potential from other potentials and artifacts. For example, U.S. Pat. No. 4,858,610 describes a method to reduce the polarization of the electrode after the delivery of stimulation. Similar techniques are described in U.S. Pat. No. 4,373,531. Other patents teach methods for enhancing the signal components of the evoked potential to make it easier to distinguish from other polarization potentials and artifacts. For example, U.S. Pat. No. 4,537,201 teaches the linearization of the exponentially decaying sensed signal by applying the sensed signal through an anti-logarithmic amplifier in order to detect the non-linear component caused by the evoked potential. Similarity between the characteristics of the evoked response and the characteristics of interfering signals, however, make it difficult to detect capture with a high degree of precision and confidence.

An alternative method has been proposed by Sholder in U.S. Pat. No. 5,476,487. Instead of isolating the evoked R-wave, Sholder proposed detecting the time periods between a pair of pacing pulses and the evoked T-wave. This method requires a specialized sense amplifier for T-wave detection. Not only is the T-wave difficult to detect, but also T-waves vary widely from patient to patient.

Housworth et al., U.S. Pat. No. 5,443,485, described a capture detection circuit for an implantable cardiac stimulator wherein the signal is integrated over a selected window of time starting at a selected delay after a stimulating pulse and applied to two comparators having different reference values. If the integrated signal exceeds a first reference value, the first comparator output goes high. If the integrated signal exceeds the second reference value, the second comparator goes high. If both comparators remain low, non-capture is indicated. If the first comparator goes high and the second comparator remains low, capture is indicated. If the second comparator goes high, an intrinsic contraction is indicated.

All of the previously described methods are more difficult to apply to the atrium than to the ventricle, both because the electrical signals generated in the atrium are weaker and because atrial signals may be masked by concurrent electrical activity in the ventricle. The detection circuits need to be accurately tuned for use in either the ventricle or the atrium. In particular, the apparatus and method of Housworth, et al. is suitable for continuous monitoring of capture. To be effective, however, the apparatus of Housworth et al. should be tuned or adjusted periodically. There remains a need, therefore, for a reliable means for tuning apparatus for detecting capture in the heart, in either the atrium or the ventricle or both. To do this, our invention uses an apparatus for detecting an impedance characteristic of the heart associated with capture rather than an evoked electrical signal as more particularly described in our co-pending application for "Implantable Cardiac Stimulator with Impedance Based Autothreshold" filed on even date herewith. Impedance sensing is known, but it has been used principally to control the rate of cardiac pacing, rather than to detect capture. With capture verified by the impedance apparatus, the faster, but less robust electrical response sensor can be tuned on a periodic basis to assure continued reliable assessment of capture.

Originally, pacemakers restored a normal, at rest, heart rate by providing a fixed rate or narrow range of externally programmable rates. However, these pacemakers failed to meet patients' metabolic demands during exercise. Consequently, so-called "rate adaptive" or "rate responsive" pacemakers were developed. These pacemakers sense some parameter correlated to physiologic need and adjust the pacing rate of the pacemaker. Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Among these parameters are the stroke volume of the heart and the minute volume of respiration, both parameters being inferred from impedance measurements. The stroke volume of the heart is defined as the volume of blood expelled by the ventricle in a single beat. It is equal to the difference between the end diastolic volume and the end systolic volume. In normal human subjects with healthy hearts, the stroke volume of the heart has been found to remain relatively constant over a wide range of exertion. Increases in cardiac output required to meet physiologic needs are primarily provided by increased heart rate. For certain patients with pacemakers whose heart rate is controlled by the pacemaker, increased cardiac output during exertion is provided by the heart attempting to increase its stroke volume. The stroke volume cannot increase, however, by a factor more than about two to two and a half times. Increasing the pacing rate is therefore still desired. It has been proposed to utilize the body's tendency to attempt to increase stroke volume to adjust the pacing rate of an implanted pacemaker, thereby providing an appropriate physiologic pacing rate.

For example, in Salo et al., U.S. Pat. No. 4,686,987 a stroke volume responsive, rate adjusting pacemaker is described. An AC signal is inserted through an implanted lead. The changing volume of the heart alters the impedance between the lead electrode and another electrode or the can of the pacemaker, and the changing impedance modulates the detected AC signal. By isolating the resulting amplitude envelope, an indication of the changing impedance can be obtained. This fluctuation is deemed to be a function, at least in part, of the action of the heart.

Chirife, U.S. Pat. No. 5,154,171, proposed that metabolic demands should be related to the ejection fraction, as a more accurate measure of true physiologic need. The ejection fraction is the stroke volume divided by the end diastolic volume. The stroke volume is taken to be the end diastolic volume minus the end systolic volume. The observed impedance of the heart is deemed to be a function of volume of the heart and therefore to be an indication of the desired measurements when taken at an appropriate time.

The impedance of the body, however, is not solely related to the beating of the heart. Other motions and factors also change the impedance characteristics. One example is change due to respiration. It has been proposed that the minute volume of respiration could be detected by an appropriate impedance measurement. See, for example, U.S. Pat. No. 4,901,725 entitled "Minute Volume Rate Responsive Pacemaker" to Nappholz et al.

U.S. Pat. No. 5,201,808 to Steinhaus et al., describes several attempts to detect the minute volume due to respiration in an accurate manner. Steinhaus et al. also proposes a relatively high frequency wave form as the appropriate means for measuring the spatial impedance as a function of the patient's pleural pressure. Steinhaus et al. notes that different frequencies for the testing pulse are adapted to detecting different phenomenon. That is, one range of frequency may be more appropriate for detecting changes due to heart beats, another would be more appropriate for detecting minute volume.

U.S. Pat. No. 5,197,467 to Steinhaus, et al. describes charging a capacitor and discharging the capacitor through the heart or a portion of the body for a selected brief interval. The voltage remaining on the capacitor after the period of discharge can be detected through a buffer, converted to digital information, and used to estimate the impedance of that portion of the patient's body between the cathode and anode electrodes.

In U.S. Pat. No. 5,507,785, Deno disclosed a rate responsive pacemaker, sensitive to impedance changes in the heart as an indicator of cardiac stroke volume or minute volume, wherein common interfering signals such as the intra cardiac electrogram, myoelectric signals, pacing artifacts and other pacing after potentials are reduced or eliminated from the measurement of the impedance by the use of a biphasic test signal and measurement process. The cardiac pacemaker has a signal injector which produces biphasic test pulses of very brief duration, for example, between two and fifty microseconds. The pulses are preferably of similar duration and magnitude, though of opposite polarity. They are delivered by the signal injector across a selected set of electrodes. The pulses are preferably of substantially constant current. A detector senses voltage resulting from the applied biphasic current pulses in each phase.

In U.S. Pat. No. 5,531,772, one of us (Prutchi) disclosed a cardiac pacemaker which senses varying impedance of the heart by discharging an active capacitor through an electrode implanted within the heart to a second electrode or to the case or can of the pacemaker. The active capacitor is discharged for a selected short period of time after which the voltage remaining on the capacitor is buffered for further processing. Prior to discharge of this active capacitor, however, the cardiac pacemaker samples the electrical condition of the heart or the body of the patient between the two electrodes by charging a passive capacitor. The voltage on this passive capacitor is also buffered and held in a sample and hold circuit until the active capacitor has been discharged. The voltage on the passive capacitor is subtracted from the residual voltage on the active capacitor and the resulting voltage is held in a sample and hold circuit. The voltage held in the sample and hold circuit is communicated to a microprocessor for adjustment of the rate of the pacemaker. To minimize error in the measurement of voltage discharged from the active capacitor, the selected short period of time for discharge can be varied dynamically by the cardiac pacemaker.

Any of the forgoing methods of detecting impedance changes in the heart, heretofore used to control pacing rate, could be used in connection with our invention to confirm capture. In addition any system which detects a change in the mechanical evoked response, rather than a change in the electrical evoked response, could also be used.

SUMMARY OF OUR INVENTION

Our invention solves the problems of the previous devices for detecting capture or adjusting the strength or duration of pacing pulses by using an evoked response detector to confirm capture on a cycle-by-cycle basis, allowing a safety pulse to be applied in any cycle where capture is lost but also periodically tuning the evoked response detector. Periodically, the mechanical evoked response is distinctly sensed through impedance sensing, pressure sensing, plethysmography or other suitable methods. When the electric evoked response detector is to be tuned, capture is verified by detecting the mechanical evoked response. Two pacing pulses are delivered to the heart in each cycle of a series of cardiac cycles. The first pulse is varied in strength or duration or both. The second pulse is maintained at a consistently high strength or duration to assure capture. The impedance of the heart is measured during a time window following the first pulse which is predicted to include the peak impedance of the heart following a stimulating pulse. The magnitude of the first pulse is gradually decreased until capture is lost. When the first pulse fails to captures the heart, the impedance measured during the window will change distinctly since the contraction of the heart would be caused not by the first pulse, but rather by the second, safety pulse. This procedure could also be implemented by beginning with a non-capturing first pulse and gradually incrementing the pulse until capture occurs. In either case, the heart is stimulated in each cycle, including those cycles in which the first pulse fails to achieve capture of the heart. If desired, the impedance of the heart could also be measured during a window between the first and second pulses. This impedance measurement could be used to eliminate variation in the detected impedance not attributable to the mechanical response of the heart.

As the magnitude of the first pulse is adjusted to isolate the threshold, the electrical evoked response is also monitored. The difference between the detected electrical signal following capture and the signal following non-capture is used to tune the electrical evoked response detection apparatus and algorithm. The energy of the pacing pulse can then be optimized by adjusting both strength and duration. During chronic operation after tuning, a very small safety margin for the pacing pulse is needed since capture is continuously monitored by the electrical evoked response apparatus and a safety pulse can be immediately applied if capture is lost. The safety pulse can be applied in the same cardiac cycle so that the heart beat remains controlled. During the tuning procedure, the safety pulse would always be applied since the performance of the evoked potential system is not assumed to be adequate until the tuning process is completed.

Use of both mechanical and electrical detectors permits periodic detection of the heart's stimulation threshold and use of that threshold to conserve battery power. The safety margin of a large-energy pulse is replaced by detection of the electrical evoked response followed by selective issuance of a timely safety pulse. Reliability of detection of the electrical evoked response is enhanced by periodic tuning.

These and other objects and features of our invention will be apparent to the skilled artisan from the following detailed description taken with reference to the accompanying drawings.

DETAILED DESCRIPTION OF OUR PREFERRED EMBODIMENT

We will now describe the preferred embodiment of our invention with reference to the accompanying figures. Like numerals will be used to designate like parts throughout.

Figure 1:
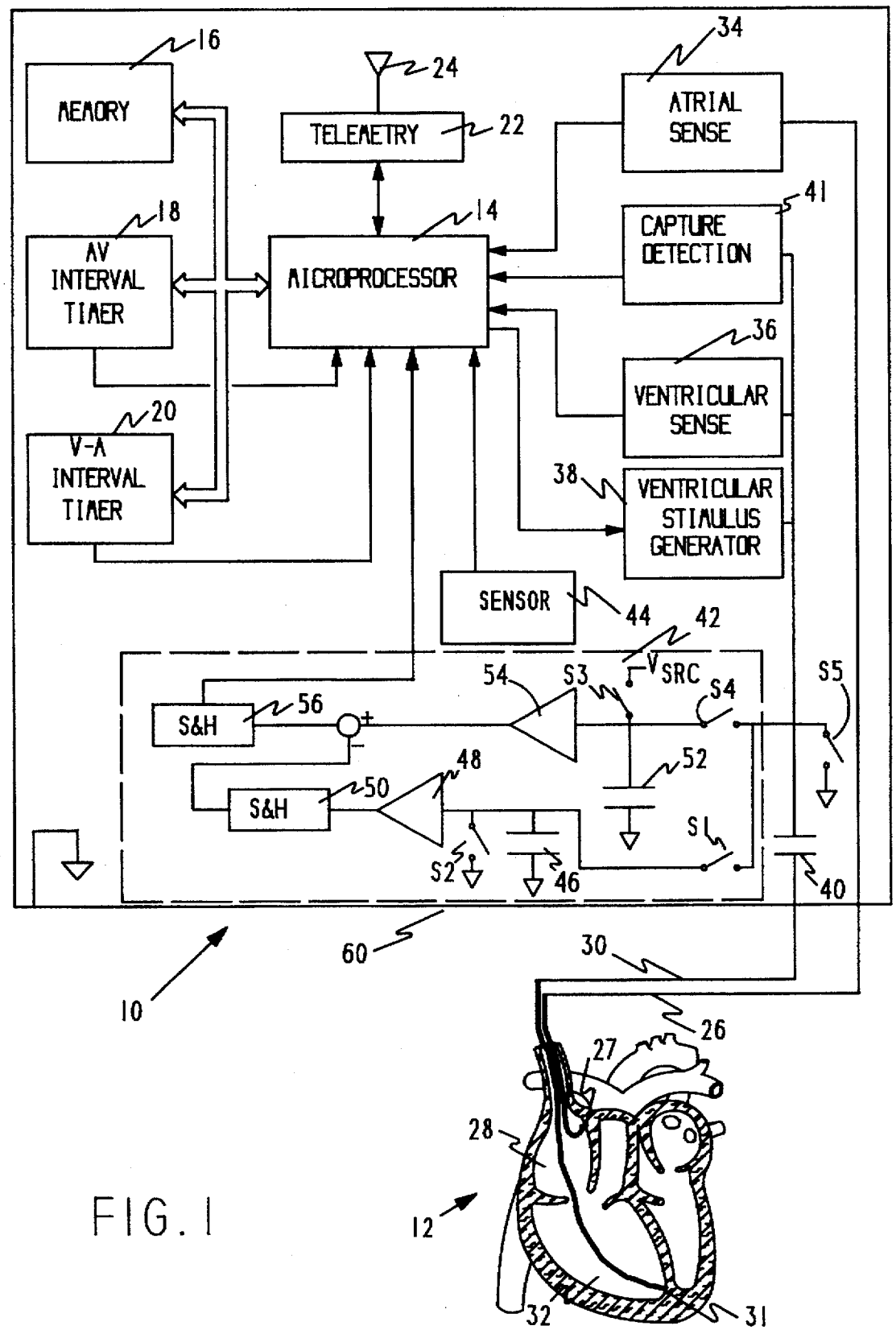
FIG. 1 is a block diagram of a first preferred embodiment of a pacemaker according to our invention.

Referring now to FIG. 1, a pacemaker, generally designated 10, is illustrated in schematic fashion with connection to a human heart 12. We have elected to describe our invention in connection with a pacemaker having atrial sensing and ventricular sensing and pacing but have illustrated capture detection and impedance circuits only in connection with the ventricle. It should be understood, however, that our invention can be employed for sensing in the atrium, the ventricle or both without departing from the teachings of our invention. In addition, the features of our invention could also be combined with an implantable defibrillator/cardiovertor.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 so that communication can be had across an antenna 24 to an external programmer (not shown). Telemetry permits an attending physician to obtain data and information from the pacemaker and to control the pacemaker to set various selectable parameters, as known in the art. A command might also be issued to the pacemaker to implement an autothreshold search sequence, as more fully explained below.

The pacemaker 10 is connected to the heart 12 through a first lead 26 to an electrode 27 in the atrium 28 and through a second lead 30 to an electrode 31 in the ventricle 32. An indifferent electrode is provided to complete the electrical circuit. In the illustrated embodiment, a can 60 or outer casing of the pacemaker serves as the indifferent electrode. Bipolar leads can also be used with our invention as well as the unipolar leads illustrated here. Atrial sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the capabilities of those skilled in the art to provide atrial pacing, should that be desired, or to provide cardioversion/defibrillation capabilities in response to the detected condition of the heart. Stimulation of the heart is passed through a coupling capacitor 40 in a conventional fashion. A switch S5, connected to ground, is periodically closed to discharge the capacitor 40 and balance stimulation pulses, producing a net zero charge at the electrode.

The microprocessor acquires information on capture through a capture detection circuit 41. As explained more fully below, the capture detection circuit 41 monitors the electrical evoked response to discriminate between capture and non-capture. If non-capture is detected, a safety pulse can be administered by the ventricular stimulus generator in the same cardiac cycle to re-capture the heart and avoid skipped beats. The microprocessor also acquires information on the condition of the heart through an impedance circuit 42. The impedance circuit 42 detects changes in impedance primarily due to the changing shape of the heart, which is related to the physical shape of the heart as it beats and pumps blood. This information can be used to detect capture of the heart by stimulating pulses as explained below. In addition to the measurement of impedance, a sensor 44 may also be provided to obtain an indication of physiologic need and adjust the pacing rate. Such a sensor may be an accelerometer, as described by Dahl, U.S. Pat. No. 4,140,132, (incorporated herein by reference) a temperature sensor, as described by Alt, U.S. Pat. No. 4,688,573 (also incorporated herein by reference), or any other suitable sensor of a parameter which may be correlated to physiologic need of the patient.

Our preferred embodiment utilizes the method and apparatus of Housworth, et al. U.S. Pat. No. 5,443,485 for detecting capture of the heart on a cycle-by-cycle basis by sensing, via an electrode placed in the heart, an electrical potential evoked in response to application of a stimulating pulse. The same electrode that is used to deliver the stimulating pulse can also be used for detecting capture. This allows use of unipolar pacing between the lead tip and the pacer can without requiring a separate ring electrode for capture detection. Alternatively, bipolar pacing between the lead tip and ring electrode can be used without requiring a third electrode. In addition, when using bipolar pacing the tip electrode can be used as the capture detection electrode.

Figure 2:
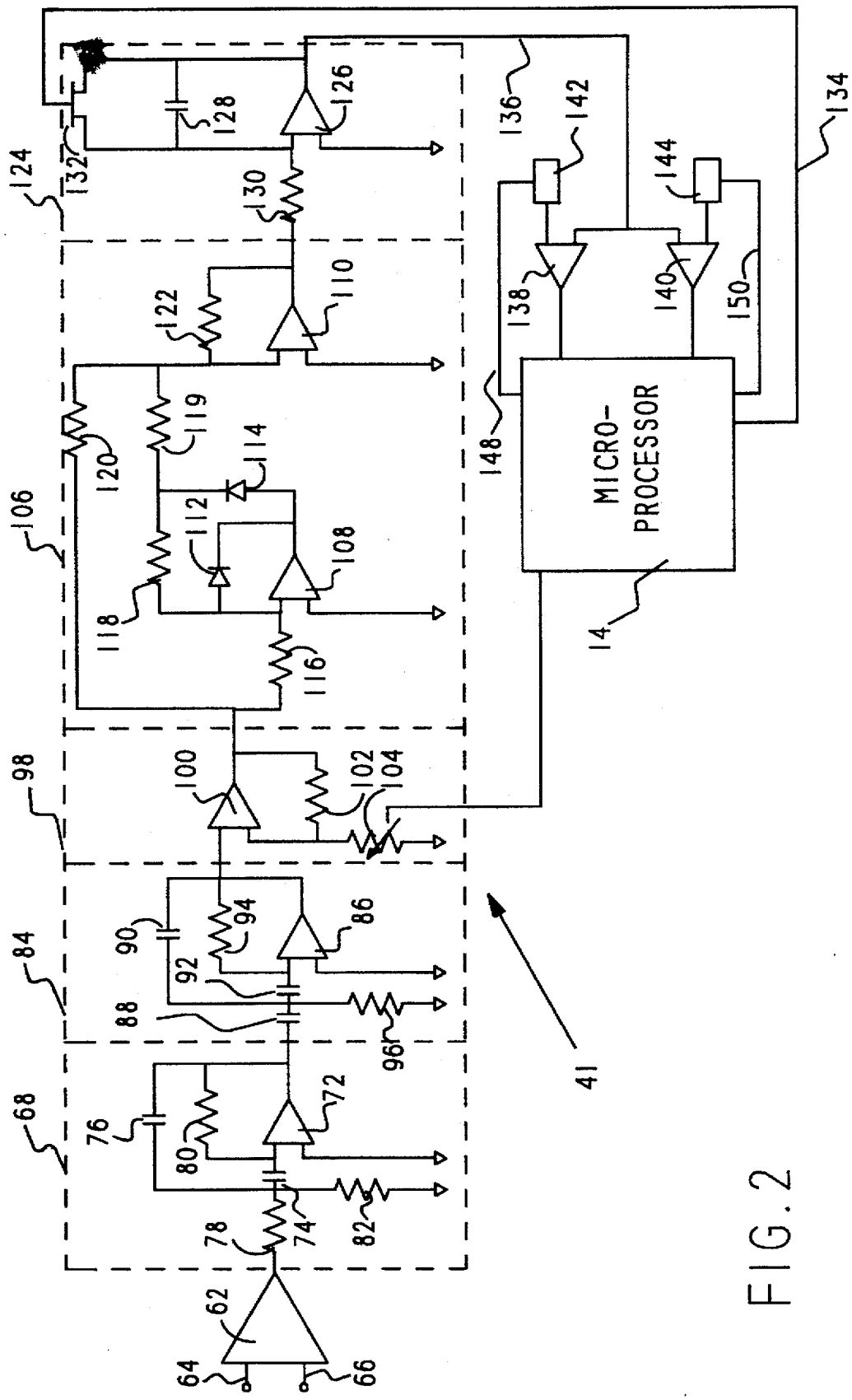
FIG. 2 is a schematic diagram of an electrical evoked response detection circuit.

Referring to FIG. 2, the capture detection circuit 41 comprises a preamplifier 62 having a pair of inputs 64 and 66 between which sensed electrical activity signals from the heart are applied. In the preferred embodiment as described herein, input 64 is electrically connected via a first conductor of an endocardial lead to a tip electrode located in the ventricle of the heart, and input 66 is electrically connected to an external conductive surface of the pacemaker housing or "can." Nevertheless, it should be understood that input 64 can also be connected to a ring electrode, with input 66 connected to the can, or input 64 can be connected to the tip electrode with input 66 connected to the ring electrode. Input 64 can also be connected to an electrode located in an atrium of the heart. The amplified output signal of pre-amplifier 62 is applied to the input of a bandpass filter stage 68. Filter stage 68 is a second-order active bandpass filter implemented by an operational amplifier 72. The bandpass characteristics and gain of bandpass filter 68 are determined by capacitors 74 and 76, and by resistors 78, 80 and 82 arranged as shown. Bandpass filter 68 has a voltage gain of 1.0, a center frequency of 37 Hz, and a Q of 0.825. The pass band is about 22 Hz to about 60 Hz.

The filtered output signal from bandpass filter 68 is applied to the input of a highpass filter stage 84. Filter stage 84 is a second-order active highpass filter implemented by an operational amplifier 86. The highpass characteristics and gain of highpass filter 84 are determined by capacitors 88, 90 and 92 and resistors 94 and 96 arranged as shown. Highpass filter 84 has a voltage gain of 1.32, a center frequency of 40 Hz and a Q of 0.707. The pass band is above about 40 Hz. It should be appreciated that bandpass filter stage 68 and the immediately following highpass filter stage 84, when considered together, are in effect a single bandpass filter with more poles of filtering on the low frequency side of the pass band, resulting in a steeper signal rolloff on the low frequency side. The pass band resulting from filter stages 68 and 84 is about 40 Hz to about 60 Hz.

The filtered output signal from highpass filter 84 is applied to the input of an amplifier stage 98. Amplifier 98 is implemented by an operational amplifier 100. The gain of amplifier stage 98, which is about one hundred, is determined by resistors 102 and 104 arranged as shown in well-known fashion. The amplified output signal of amplifier stage 98 is applied to the input of a precision full-wave rectifier or absolute value stage 106. Absolute value stage 106 is implemented by operational amplifiers 108 and 110, diodes 112 and 114, and resistors 116, 118, 119, 120 and 122 arranged as shown. The gain of the amplifier is controlled by the microprocessor. Switched capacitors may be used for the resistors. By controlling the switching rate, the effective resistance can be controlled. Additional information on switched capacitor circuits in implantable medical devices is found in U.S. Pat. No. 4,913,145 to Stotts.

The rectified output signal of absolute value stage 106 is applied to the input of an integrator stage 124. Integrator 124 is implemented by an operational amplifier 126. The integrating characteristics of integrator stage 124 are determined by capacitor 128 and resistor 130 arranged as shown. An FET transistor switch 132 is connected in parallel with integrating capacitor 128 such that the drain terminal of FET 132 is connected to one terminal of capacitor 128 and the source terminal of FET 132 is connected to the other terminal of capacitor 128. Integrator 124 can be "cleared" by applying an appropriate signal to the gate terminal of FET 132 via line 134 to switch FET 132 on, thereby providing a conduction path between the source and drain terminals through which capacitor 128 is discharged.

The integrated output signal of integrator stage 124 is applied via line 136 to one input of each of two comparators 138 and 140. Each of the other inputs of comparators 138 and 140 are connected to variable reference voltage sources 142 and 144, respectively. The reference voltage source 142 of the first comparator 138 is set at a voltage level lower than that of the reference voltage source 144 of the second comparator 140. The output signal of each of comparators 138 and 140 is applied to a separate input of control logic and microprocessor 14. microprocessor 14 also has an output connected to line 134 for providing a signal to control the resetting, or clearing, of integrator stage 124 as described above. In addition, microprocessor 14 also has outputs connected to lines 148 and 150 to provide control signals for setting the reference voltage levels. While blocks 68, 84, 98, 106 and 124 are illustrated as being implemented by operational amplifiers with conventionally arranged discrete resistors and capacitors, it should be noted that the values of the passive components required may result in discrete components having physical sizes that are undesirably large in view of the generally recognized desirability of minimizing the overall size of implantable cardiac stimulators. It is therefore preferred that the illustrated functional blocks be implemented in an integrated circuit using known switched-capacitor technology.

Figure 3:
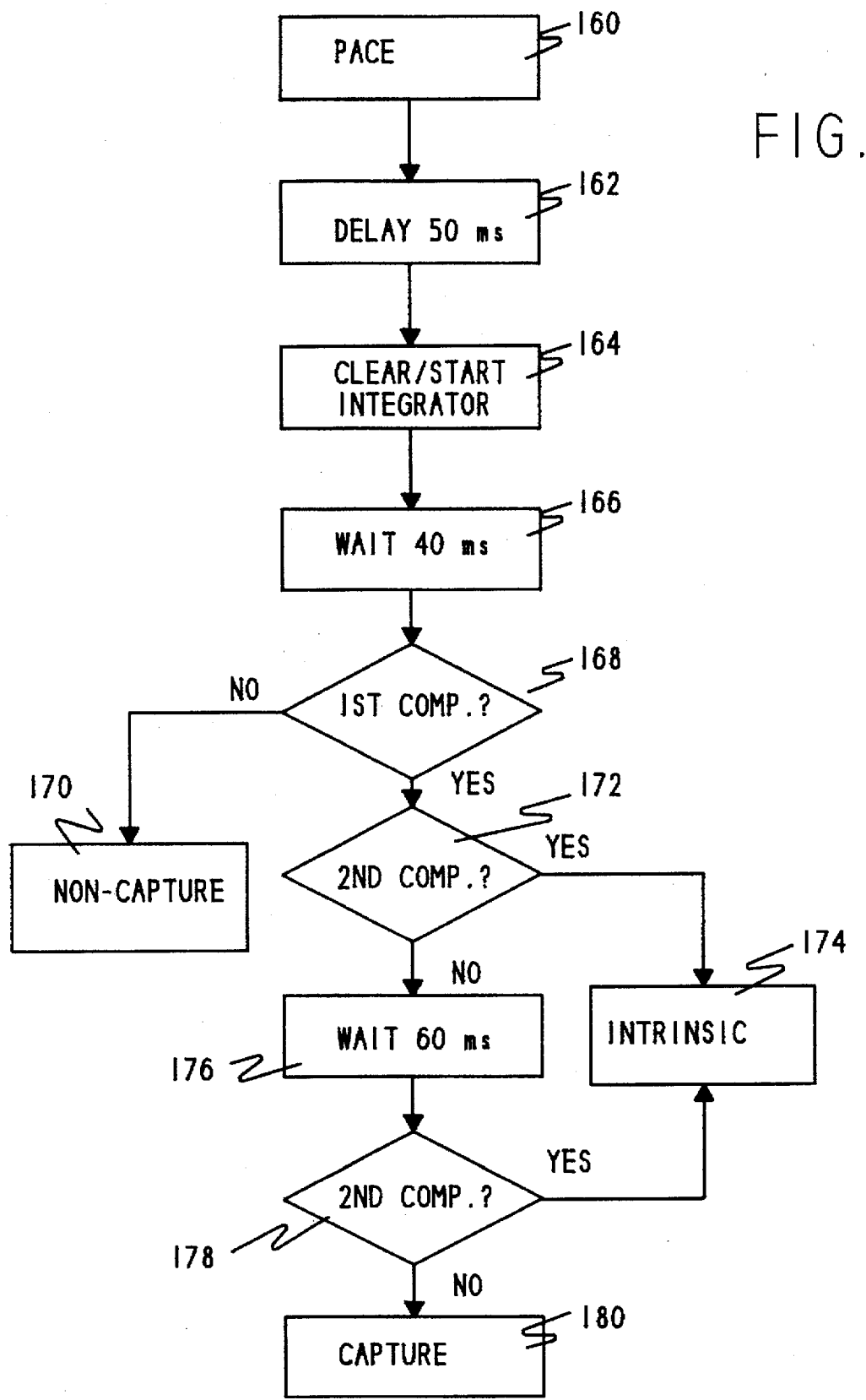
FIG. 3 is a flow chart of an algorithm for application with the electrical evoked response detection circuit of FIG. 2.

Referring now to FIG. 3, there is illustrated a flow chart of the operation of control logic and microprocessor circuit 14, with reference to the circuit of FIG. 2. Starting at the top of the flow chart, the process of capture detection begins with delivery of a pacing pulse by the cardiac stimulator 10, indicated by box 160. Logic circuit 14 uses the pacing event as a marker from which subsequent timing is counted. Following the pacing event, there is a controllable delay of about 50 msec, as indicated by box 162. At 50 milliseconds after the pacing event, a signal is generated on output line 134 to clear integrator 124 and begin a new integration period, as indicated by box 164. After having been cleared, integrator 124 continues integrating over an initial time window of controllable length, usually about 40 msec, as indicated by box 166. At the end of the first time window, logic circuit 146 checks the output of first comparator 138 to determine whether the first comparator threshold (i.e. reference voltage 142) has been exceeded, as indicated by decision box 168. If the answer is no, then it is determined that capture has not occurred as indicated by process block 120. If the answer is yes, it is tentatively determined that capture has occurred, but it is possible that the threshold of first comparator 138 has been exceeded due to the occurrence of an intrinsic contraction during the initial integration window rather than an evoked response indicative of capture. To identify intrinsic contractions, which tend to generate signals of much greater amplitude than evoked responses, control microprocessor 14 checks the output of second comparator 140 to determine whether the threshold of second comparator 140 (i.e. reference voltage 144) has been exceeded, as indicated by decision box 172. If the answer is yes, then it is determined that an intrinsic contraction has occurred, as indicated by box 174. If the answer is no, then the integrator 124 is permitted to continue integrating for an additional period, usually about 60 msec, as indicated by box 176. At the end of the extended integration window, control logic circuit 14 checks the output of second comparator 140 again to determine whether the threshold of second comparator 140 (i.e. reference voltage 144) has been exceeded, as indicated by decision box 178. If the answer is no, meaning that the output of integrator 124 exceeded the threshold of the first comparator 138 within 90 msec after the stimulating pulse, but did not exceed the threshold of the second comparator 140 within 150 msec after the stimulating pulse, then it is determined that capture has occurred, as indicated by box 180. If the answer is yes, meaning that the output of integrator 124 exceeded the threshold of first comparator 138 within 90 msec after the stimulating pulse, and exceeded the threshold of second comparator 140 within 150 msec after the stimulating pulse, then it is determined that an intrinsic contraction has occurred, as indicated by box 174.

Further details on the operation of the capture detection circuit 41 can be found in U.S. Pat. No. 5,443,485, which is incorporated herein by reference. As noted in the '485 patent, it is difficult to generalize the preferred levels for the first threshold for the first comparator 138 and the second threshold for the second comparator 140 since the signal levels involved will be highly dependent upon the overall gain characteristics of the particular implementation of the circuit of FIG. 1 in combination with the lead system used to sense heart activity. It has been found, however, that signal at the output of the integrator stage tends to be about an order of magnitude greater in the case of an intrinsic contraction as compared to a signal indicative of capture. Thus, for example, if the first capture threshold is set at 100 millivolts, the second capture threshold should be set at about 1 volt. Even for a given hardware system, there may be some patient to patient variation in optimal threshold level settings and also variation in the same patient over time. It is therefore desirable that control microprocessor 14 be configured to permit a range of adjustment of reference voltages 142 and 144, which implement the threshold levels. Periodic automatic tuning is described hereafter.

It should also be understood that the integration time windows as disclosed herein are the preferred windows for the disclosed filter characteristics and lead arrangement, but other time windows may be preferable with other implementations. Moreover, autotuning may involve changes in the time windows. There may also be some patient-to-patient variation and variation in the same patient over time that requires shifting the time windows for optimum results. It is therefore desirable that microprocessor 14 be configured to permit a range of adjustment of the start time of the integration windows, and of the times at which the comparator outputs are checked. Periodic automatic tuning is described hereafter. For example, it has been observed that with signal data collected from a bipolar lead system, as opposed to the disclosed unipolar system, better discrimination between capture and non-capture is obtained by shifting the windows about 5 milliseconds earlier.

To implement periodic automatic tuning of the capture detection circuit 41, an alternative, independent means for confirming capture must be provided. Because such alternative means is used only periodically it can be more energy costly and have a slower response time. It should, however, be reliable and stable. To provide alternative capture detection means we have utilized the impedance circuit 42.

The impedance circuit 42 comprises a first capacitor 46 which we will call a passive capacitor. This capacitor is connected to the lead 30 through a switch S1 and to ground through a second switch S2. The capacitor is also connected to a buffer 48 in common with the two switches S1 and S2. On the other side of the capacitor 46, the capacitor 46 is connected to ground. The buffer 48 communicates with a sample and hold circuit 50. The function of the separate sample and hold circuit 50 can be performed by the passive capacitor 46 and the buffer 48, if the sampling time (see FIG. 4) is short and the impedance of the buffer 48 is high. Each of the two switches S1 and S2 and the sample and hold circuit 50 are controlled by the microprocessor 14. Such connections are well known in the art and are not illustrated for the sake of clarity. A second capacitor 52, which we will call an active capacitor, is also connected to the lead 30 through a switch S4. Preferably, the passive capacitor is of similar magnitude to the active capacitor, and most preferably the passive capacitor has the same capacitance as the active capacitor. This enables the passive capacitor to serve as an accurate model of the effect of background voltages on the active capacitor, as will be more fully explained below.

The side of the active capacitor 52 connected to the lead is further connected through a switch S3 to a voltage source, labeled $V_{SRC}$ in FIG. 1. Finally, the capacitor 52 is connected in common with the two switches S4 and S3 to a buffer 54. The other side of the capacitor 52 is connected to ground. The output of the buffer 54 is combined with the output of the sample and hold circuit 50, as will be more particularly described below, by subtracting the voltage of the sample and hold circuit 50 from the output of the buffer 54. The resulting voltage is held in a second sample and hold circuit 56 until required by the microprocessor. Typically, the analog value of the voltage held by the sample and hold circuit 56 is converted to a digital value for further processing. As explained above, the switches S3 and S4 and the sample and hold circuit 56 are controlled by the microprocessor 14 in a manner similar to that of switches S1 and S2 and sample and hold circuit 50.

Figure 4:
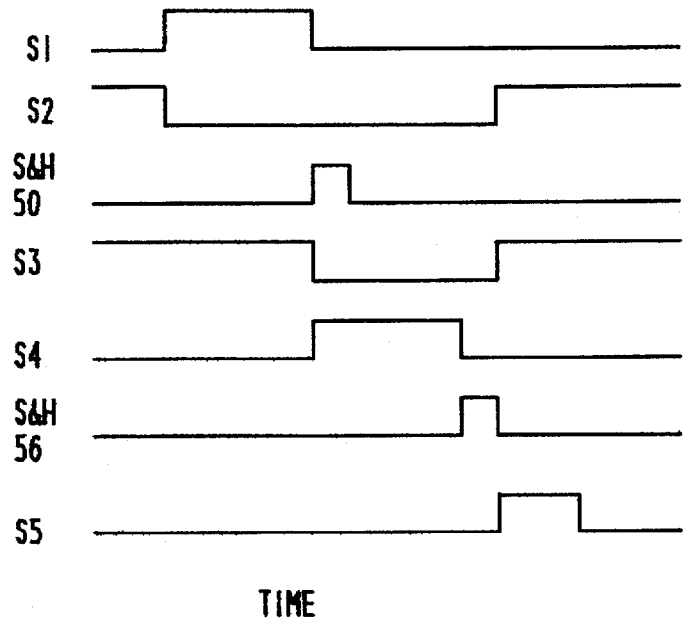
FIG. 4 is a timing diagram.

The operation of the impedance circuit 42 can be understood with respect to a timing diagram, FIG. 4. As explained in U.S. Pat. No. 5,531,772, the impedance circuit determines the impedance of the heart at a relatively high rate, on the order of 100 to 300 sample cycles per second when used in connection with pacemaker rate control. For autothreshold, a short period or window of about 10 msec, at a selected time or delay after delivery of a stimulating pulse is used. The delay is on the order of 120 to 250 msec. A single sample cycle is described with respect to FIG. 4. As each cycle begins, passive capacitor 46 is in a discharged state while active capacitor 52 is charged to a preselected voltage level, $V_{SRC}$, which may be about 0.5V or less. Initially, during the cycle, S1 is closed for a preselected period, for example, 15 μsec. This is indicated in the timing diagram of FIG. 4 by the line S1 going high. Simultaneously, switch S2 is opened as indicated by the line S2 going low. This effectively connects the passive capacitor 46 through the lead 30 to the electrode 31 within the heart 12. The passive capacitor 46 assumes the electrical value of the electrode 31 during the time that switch S1 is closed.

After switch S1 opens, the electrical condition of the passive capacitor 46 appears through the buffer 48 at the sample and hold circuit 50. The sample and hold circuit 50 is therefore triggered by the microprocessor to capture this voltage as indicated by the line S/H 50 going high. While the passive capacitor 46 is charged from the electrical condition of the heart, the active capacitor 52 is charged from $V_{SRC}$ through S3 as indicated by the high condition of line S3 in FIG. 4. When switch S1 opens, switch S3 also opens as indicated by the low condition of line S3. Simultaneously, switch S4 closes, as shown by line S4 in FIG. 4, for a preselected period of time, for example 15 μsec. If the active capacitor 52 has the same capacitance as the passive capacitor 46, as described above, and if the resistance of the two switches S4 and S1 are equal, then S1 is preferably activated for the same length of time as S4. The active capacitor 52 discharges through switch S4 and lead 30 through the electrode 31 in the heart. Electrical current passes from the electrode 31 within the heart to an anode on lead 30 or to the can 60 of the pacemaker which acts as an indifferent electrode.

When S4 opens, S3 does not immediately close. Rather, the electrical condition of the active capacitor 52 is passed through buffer 54. The electrical value retained in the sample and hold circuit 50, representing the electrical condition of the heart, is subtracted from the output of buffer 54 and the resulting value is captured by the sample and hold circuit 56, as represented by line S/H 56 going high. After the sampling by sample and hold circuit 56 is complete, initial conditions on the capacitors 46, 52 can be restored by connecting the passive capacitor 46 to ground through S2 (indicated by line S2 going high) and the active capacitor 52 to $V_{SRC}$ through switch S3 (indicated by line S3 going high). In addition, pacing and impedance sensor pulses are usually passed to the heart through an AC-coupling capacitor 40. Switch S5 is used to discharge this capacitor and to produce a balanced pulse which results in zero net charge flow through the tissue. This is indicated by line S5 going high, closing switch S5. Switch S5 opens when line S5 goes low.

S4 being closed (see FIG. 4) represents a selected short period of time during which the active capacitor 52 is discharged through the heart. The voltage on the active capacitor 52 decays exponentially according to the following formula:

$$V_{CA}(t)=V_0 e^{-t/RCa}$$

Where $V_{CA}$ is the voltage remaining on the active capacitor after a time t; $V_0$ is the initial voltage on the capacitor; R is the lumped resistance of the circuit, and Ca is the capacitance of the active capacitor 52. There is an error associated with making the measurement of $V_{CA}$ as there is in making any measurement. This error can be minimized, however, by making the measurement after an elapsed time T equal to one time constant that is, at t=T=RCa. The desired measured value is R determined as follows:

$$R=-t/(Ca\ ln(V_{CA}(t)/V_0))$$

The fractional error in the measurement of R, that is, d(ln R), is a function which has a minimum at t=T=RCa. The function is:

$$d(ln\ R)=-[ln(V_{CA}(t)/V_0)]^{-1}[V_{CA}(t)/V_0]^{-1}$$

Figure 5:
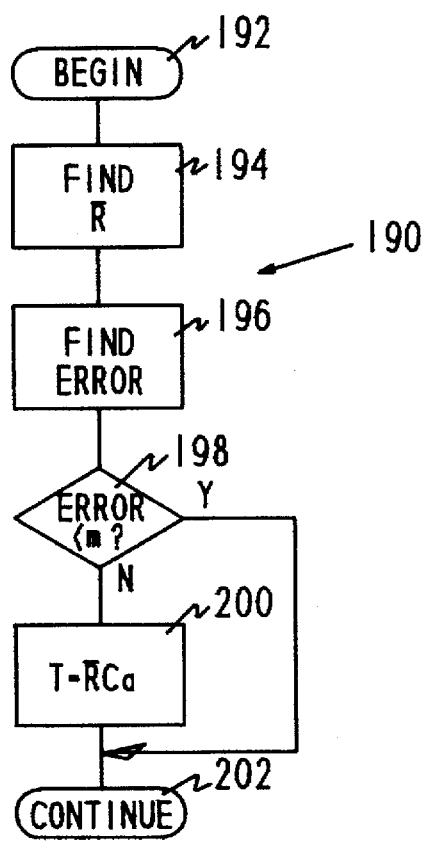
FIG. 5 is a flow chart of an algorithm for minimizing error in voltage measurement on an active capacitor.

The value Ca, the capacitance of the active capacitor, is constant, but the value R, the impedance of the circuit including the heart, is changing. The error associated with the measurement of $V_{CA}$ (and thus also the error associated with the impedance) can be minimized by programming the microcomputer 14 to dynamically adjust the time during which S4 is open. A suitable procedure, generally designated 190, is illustrated diagrammatically in FIG. 5.

The procedure 190 is part of the general operation of the microprocessor 14. When the procedure 190 begins 192, an average or representative value of the impedance R is determined 194. This could, for example, be the rolling average of the measured value of the impedance for a predetermined number of cycles. The fractional error d(ln R) is then computed 196. The fractional error is compared 198 to an acceptable value m. If the fractional error is less that the acceptable value m, the value t, that is the time switch S4 is open, is unchanged. If the fractional error is greater than the acceptable value m, a new value of t is calculated 200 such that t=RCa. The microprocessor proceeds 202 with other processing, using the new value t to determine the impedance from the measured value of $V_{CA}$ after a discharge time t.

Figure 6:
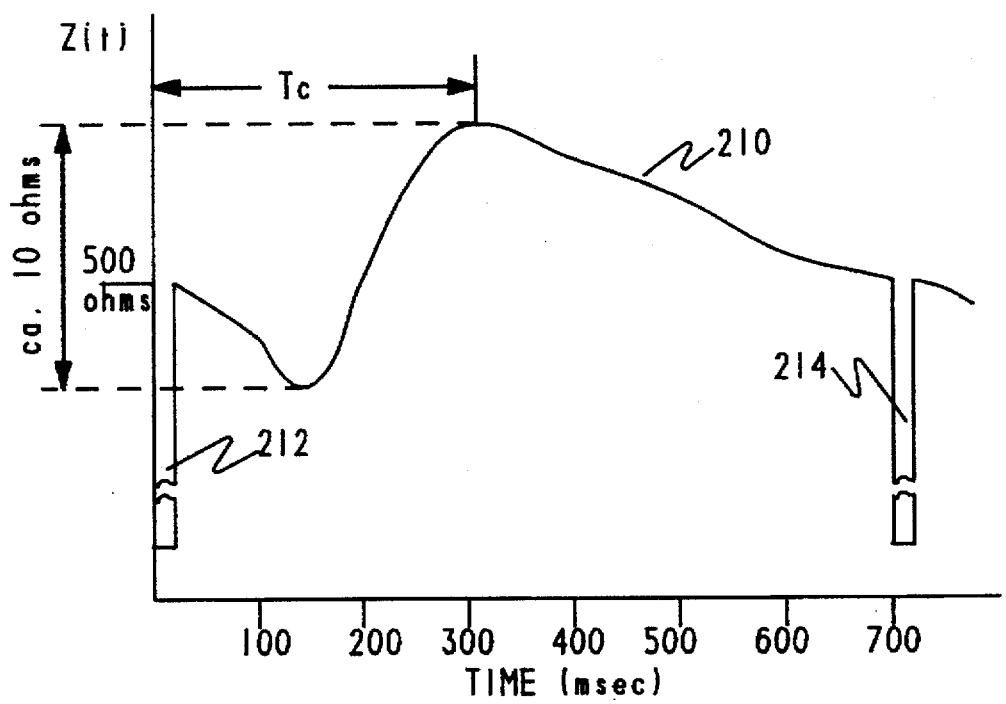
FIG. 6 is a graph of impedance after a stimulating pulse.
Figure 7:
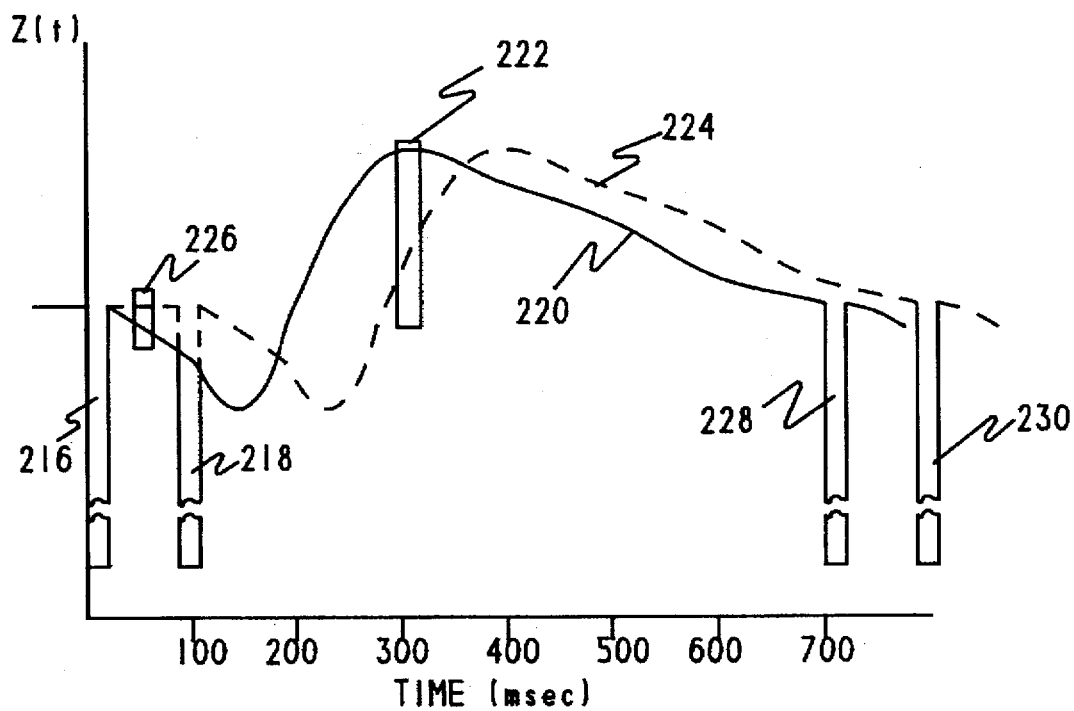
FIG. 7 is a graph of impedance using dual pulses.

Use of recognition of a mechanical response to stimulation for autothreshold adjustment can best be understood by reference to FIGS. 6 and 7. FIG. 6 illustrates a graph of the impedance response 210 of the heart over a cardiac cycle, in response to a pacing pulse 212. The pacing pulse 212 is assumed to be of a magnitude such that the heart is captured. The result is a varying impedance, associated with the mechanical pumping action of the heart which varies over about a 10 ohm range around an average impedance of about 500 ohms. After the pacing pulse 212, the impedance declines as the heart contracts and then rises again as the heart fills with blood. This refilling process lasts for about 300 msec after the delivery of the pulse 212, or for a time $T_C$. After a delay associated with the rate of pacing, a second pace 214 would restimulate the heart, causing another contraction. It is initially desired to determine on a case by case basis the approximate length of time $T_C$ between a pacing pulse and a selected impedance feature. This would be accomplished by applying a pacing pulse in several cycles and measuring both the impedance and elapsed time. When the impedance experienced a local maximum, the time $T_C$ would be determined. This process would preferably be conducted over several cycles and the average of the measured $T_C$ would be utilized as a delay factor in the next part of the procedure. Having determined a best estimate for $T_C$, the pacemaker would then determine the threshold, as illustrated in FIG. 7. A pair of pulses P1 and P2, such as pulses 216 and 218 would be delivered to the heart in each cardiac cycle by the pacemaker 10. The leading pulse 216 would be variable in either duration or strength (e.g. voltage) or both. The second or trailing pulse 218 would be of such strength and duration as to assure capture. In the course of implementing our invention, the leading pulse 216 could be either incremented or decremented as to either strength or duration, or both. Assuming that the leading pulse 216 is decremented, the pulse would initially be applied with a strength and duration great enough to assure capture of the heart. In such a situation, impedance of the heart would be detected approximately as shown by line 220. A measurement window 222 is established after the delivery of the leading pulse 216 after delay either equaled to or proportional to the predetermined time $T_C$. Note that $T_C$ could also be selected by programmer action, utilizing the external programmer. The window 222 is of relatively short duration, on the order of 10 msec. So long as the leading pulse 216 stimulates the heart, the detected impedance during period 222 would be small. As soon as the voltage of 106 declines below the threshold so that the heart is no longer stimulated to contract by the first pulse 216 the detected impedance is displaced as shown by the dotted line 224. Measurement of impedance during the sampling window 222 shows a sharp change. This phenomenon is attributable to the failure of the first pulse 216 to capture, followed by capture of the heart by the second pulse 218.

In addition to the measurement window 222, impedance can also be measured during an initialization window 226. Subtracting the impedance measured during the initialization window 226 from the impedance measured during the sampling window 222 operates to eliminate the background or normal impedance of the body, which, as mentioned heretofore, would usually be on the order of 500 ohms. The value detected during the window 226 would be subtracted from the impedance measured during the sampling interval 222. The resulting difference would be more easily compared to recognize the shift due to failure of the first pulse 216 to capture. Thereafter another cardiac cycle would be commenced with two more pulses 228, 230.

It is desirable to determine the optimum strength and duration of a pacing pulse, as explained, for example, in U.S. Pat. No. 4,979,507. To do this, a series of tests would be performed setting the duration of the first pulse 216 to a given initial value and then varying the amplitude or voltage of the pulse 216 until loss of capture is detected, followed by incrementing or lengthening the duration of the first pulse 216 and again decrementing the magnitude of the first pulse 216 until capture were lost. A series of these tests would enable the microprocessor 14 to approximate the strength duration of the curve and, as explained in U.S. Pat. No. 4,979,507, determine the optimum pacing duration and strength. It will be noted that the same result could be achieved by incrementing the first pulse 216 until capture were achieved and could also be achieved by decrementing the duration of the first pulse 216.

Figure 8:
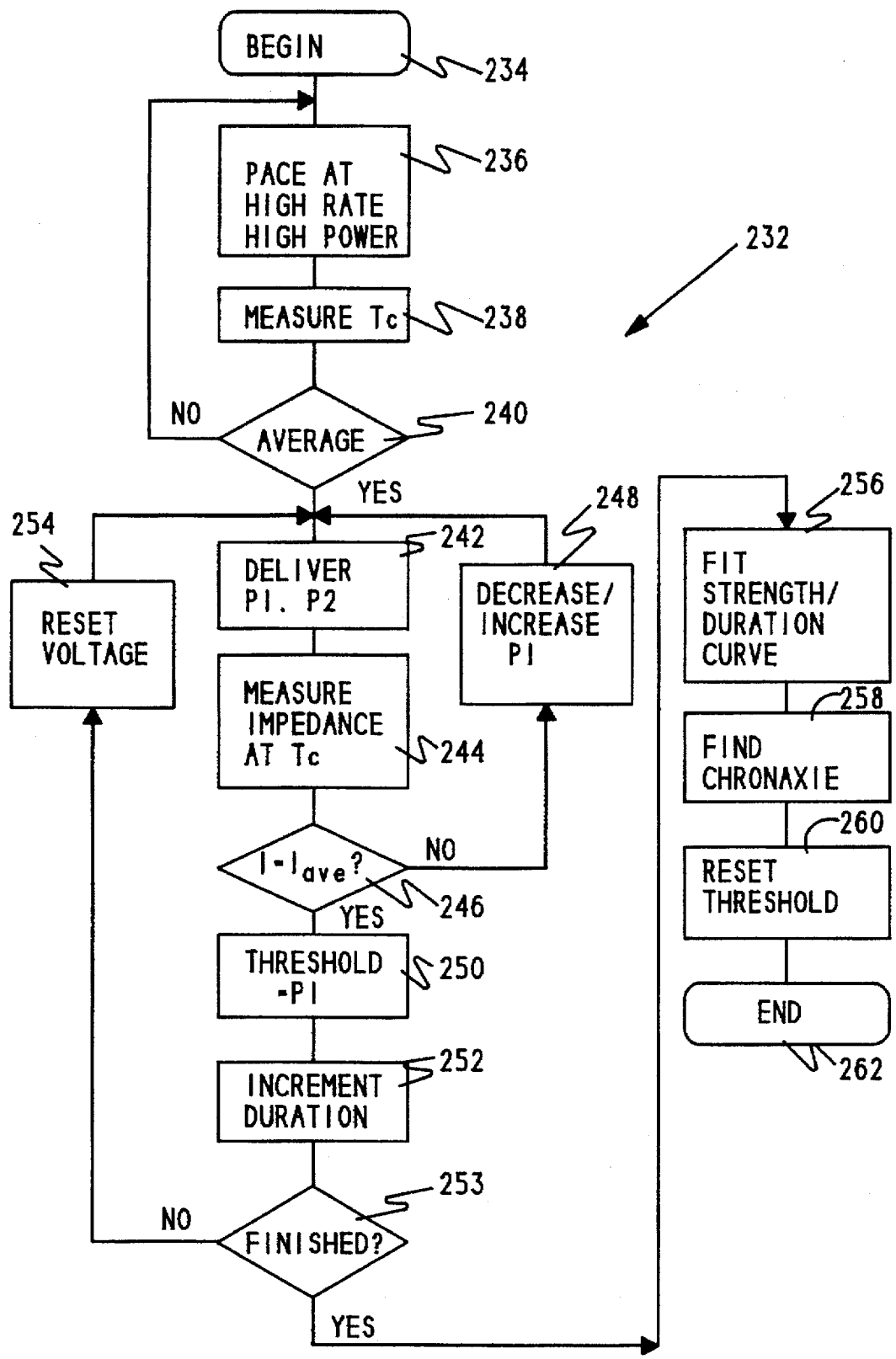
FIG. 8 is a flow chart of an algorithm for implementing a mechanical response detection.

FIG. 8 illustrates a software program 232 which could be implemented on microprocessor 14 to detect capture according to our invention. The software program 232 would be executed by the microprocessor 14 either in response to detected changes (see Schroeppel, U.S. Pat. No. 5,413,592) or on a regular basis, for example, once a day, or in response to a command from an external programmer. The software program 232 would begin at 234 and would proceed to pace 236 the heart at a selected high power to assure capture, and at a rate, such as a high rate, that would assure that the action of the heart did not itself interfere with the test. By observing the rising impedance, as mentioned above, $T_C$ would be measured 238. $T_C$ represents the period of time from the pacing pulse to a distinguishing characteristic of the impedance waveform, preferably but not necessarily, the detected maximum impedance. Preferably this process would be repeated over several cycles until a suitable average 240 had been obtained. After initialization, measurement of the pacing threshold would commence with the delivery 242 of two paired pulses P1 and P2 corresponding to the first pulse 216 and the second pulse 218 of FIG. 7. Additional impedance could be measured during a first window 226 either after or between the two pacing pulses P1 and P2. After a delay of $T_C$ following either the first or second pacing pulses 216, 218, and in the illustrated instance following the first pacing pulse 216, the impedance of the heart would be measured 244. This impedance might then be used without further alteration or the initial impedance during first window 226 could be subtracted in order to eliminate or reduce other effects. The microprocessor 14 would then determine 246 if the detected impedance or difference in impedance was substantially equal to the average impedance or average difference in impedance determined as explained above. If they are equal, within a preselected error, it would be assumed that capture had not been lost by the first pulse 216 and the voltage of that pulse 216 would be decremented 248. It will be apparent, of course, that the first pulse 216 could also be made very much smaller than the expected threshold and incremented until capture was achieved by the first pulse without departing from the teachings of our invention. In that case, of course, the voltage of P1 would be increased.

When the measured impedance suddenly and markedly changes from the measured average impedance, the microprocessor 14 stores 250 a threshold value equal to the magnitude of the pacing pulse P1. This value could be used for a rough approximation of the threshold, but is would also be possible to more accurately determine the optimal pacing strength and duration by utilizing the chronaxie. Assuming it was desirable to use the chronaxie, the duration of the first pulse 216 would be extended 252 (or decremented depending on the preference of the programmer) in a step wise fashion throughout a preselected range of durations. For each duration an associated threshold voltage would be determined by the microprocessor inquiring 253 whether the range of durations had been investigated and, if not, resetting the voltage 254 of the first pulse 216 and preceding to deliver another series of pulses of P1, P2 until a threshold associated with that duration had been determined. After the entire range had been sampled, microprocessor 14 would fit 256 a strength duration curve and then calculate 258 the chronaxie as explained in U.S. Pat. No. 4,979,507. From this determination, an optimum effective strength and duration will have been selected for the operation of the pacemaker and those values of both duration and strength would be used to reset 260 the threshold plus a desired safety margin. This portion of the microprocessor programming would then end 262.

Figure 9:
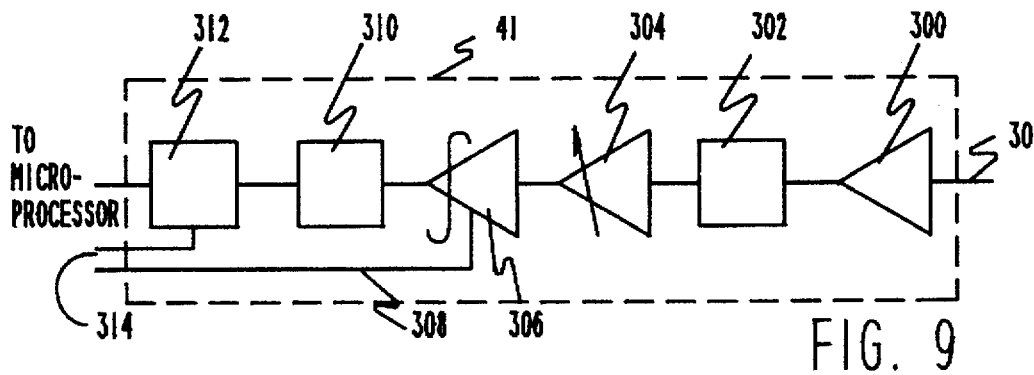
FIG. 9 is a block diagram of an electrical response detection circuit.

The two-pulse impedance technique for identifying capture is accurate, reliable, but energy expensive. As a practical matter, because of power limitations, it can only be used infrequently. On the other hand, sensing of the evoked potential requires little energy and can be performed chronically. To be accurate, however, sensing of the evoked potential should be tuned from time to time to the particular patient and to the particular patient's condition. Otherwise, electrical noise, changes in patient condition, and other factors could so reduce the accuracy of evoked potential detection as to render it useless. We will now describe the evoked potential capture detection, and autocalibration apparatus and sequence of our invention. The capture detection circuit 41 is illustrated in FIG. 1 connected to the heart 12 through the lead 30 and to the microprocessor 14. Further detail of the capture detection circuit is given in FIG. 2 and explained above. For clarity the capture detection circuit 41 is also shown in block diagram form in FIG. 9. The capture detection circuit 41 comprises a front end amplifier 300 which receives the signal from line 30 and transmits the amplified signal to a filter 302. A variable gain amplifier 304 further amplifies the signal and passes the signal to an integrator 306. The integrator 306 is controlled through its reset line 300 by the microprocessor 14. Signals on the reset line 308 control both the initiation of integration and the duration over which integration takes place. In the capture detection circuit 41, therefore, there are three variables, all controlled by the microprocessor 14: the gain of the variable amplifier 304 and both the integration delay, or beginning of integration, and the integration window, or the duration during which integration takes place. After the integrator 306, the integrated signal passes to a threshold comparator 310. If as a result of integration a signal exceeds a predetermined threshold, a digital latch 312 is set, indicating a logical true condition. The latch 312 can be reset 314 by the microprocessor.

Figure 10:
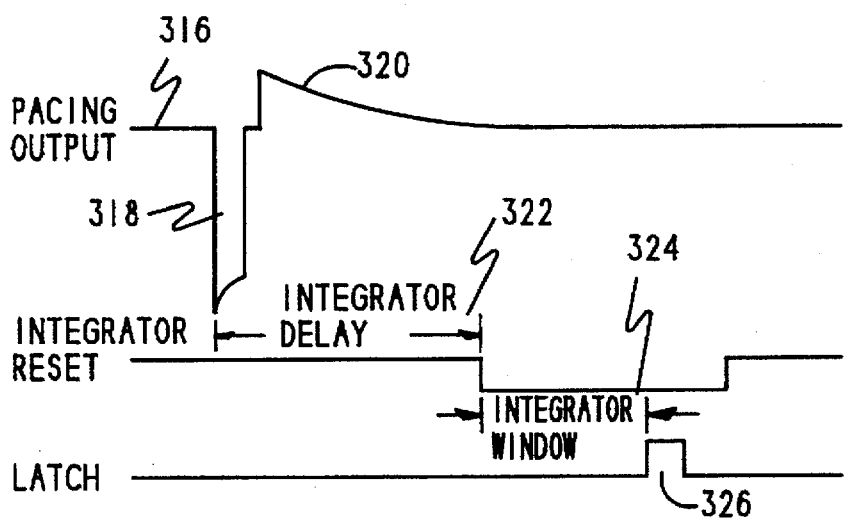
FIG. 10 is a timing diagram.

A timing diagram for a capture detection circuit 41 is illustrated in FIG. 10. A pacing output 316 can be produced, for example, by the ventricular stimulus generator 38. It will be understood by those skilled in the art that the techniques described herein are equally applicable to atrial and ventricular chambers and that an atrial stimulus generator, with associated capture detection circuit could be provided with the atrial sense circuit 34 illustrated in FIG. 1. The pacing output 316 ordinarily comprises a pacing pulse 318 followed by a balancing discharge 320 of opposite polarity, lower magnitude and longer duration which balances the charge output at the electrode, as well known in the art. This balancing pulse 320 and after effects of the pacing pulse 318 inhibit sensing of the evoked potential which is indicative of the actual contraction of the heart as a result of the pacing pulse 318. It is therefor advisable to introduce an integration or integrator delay 322. After the integrator delay 322, an integrator window 324 is initiated during which the evoked electrical signal of the heart is integrated. If the resulting value is sufficiently large, this is indicative that capture has in fact taken place and the latch 326 can be set indicating capture.

Figure 11:
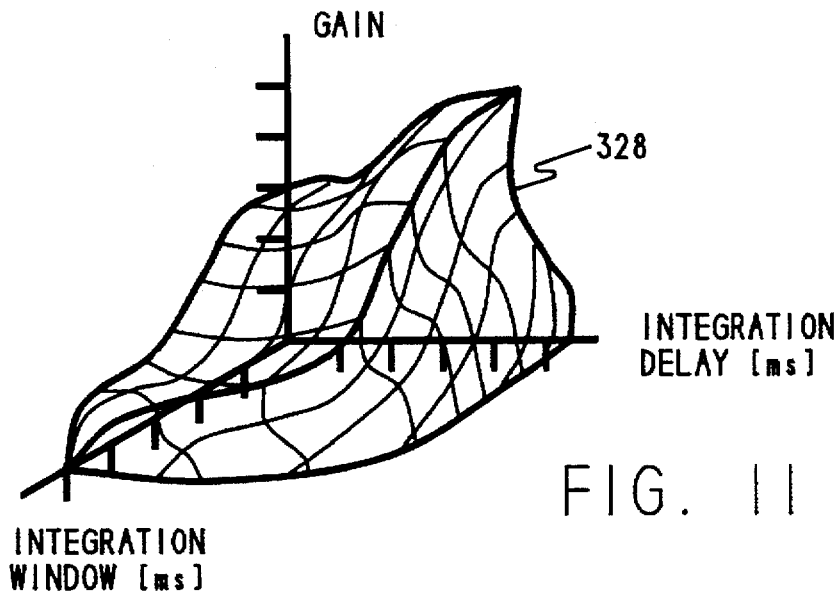
FIG. 11 is a graphical representation of valid parameters for the electrical response detection circuit of FIG. 9.
Figure 12:
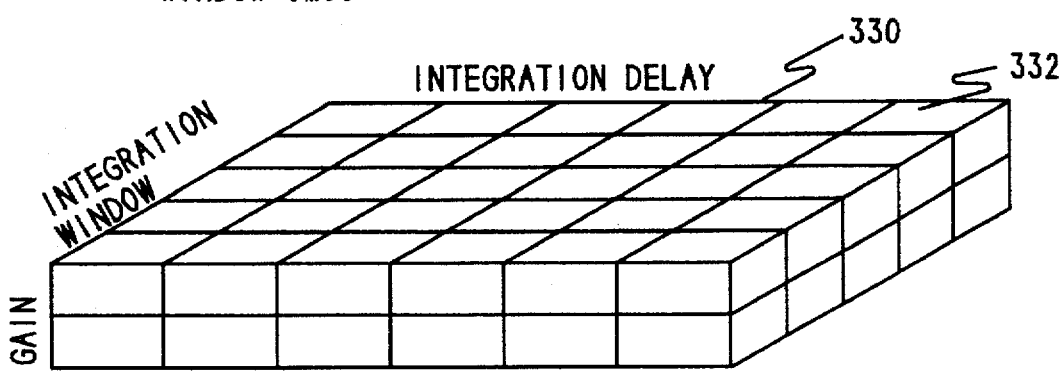
FIG. 12 is a graphical representation of a memory map.

True capture, sometimes called massive capture, occurs when enough cells are stimulated so that contraction propagates throughout the muscle of a heart chamber. It is possible, however, for a pacer pulse to produce only local capture, that is, stimulation of a few cells surrounding the electrode, but insufficient to propagate to other tissue. This condition can be falsely detected as massive capture by a capture detection circuit 41 if the capture detection circuit is not properly tuned. For example, if the gain of the amplifier 304 is set too high, the relatively small evoked signal resulting from local capture might appear to be the larger signal resulting from massive capture. If even higher gain is used, the pacing artifact might appear to be the result of capture, that is, the pacer might falsely interpret the pacing artifact as an evoked response. In connection with a particular pacemaker, it can be empirically determined using an evoked potential CD cell which combinations of parameters do not cause a false indication of capture due to the detection of the pacing artifact. Graphically, this condition is illustrated in FIG. 11. The three controlled parameters of the capture detection circuit 41, gain, integration delay and integration window, are shown on orthogonal axes. A boundary surface 328 can be determined. If the values of the gain, integration delay and integration window are within this surface, a false positive indication of capture due to the existence of a pacing artifact would not be expected. Settings outside the boundary 328 would be expected to result in false positive readings, that is, an indication that massive capture had been achieved when in fact it had not. Acceptable values for the gain, integration window and integration delay can be stored in memory 16 in the pacemaker. Such a memory map or truth table 330 is illustrated in FIG. 12. The memory map 330 comprises memory locations for different settings of gain (two different settings are illustrated but more could be selected); for values of the integration window (five discrete settings are illustrated); and for integration delay (six settings). In each of the cells 332, a logical true or false value would be placed indicating whether that particular combination of gain, integration window, and integration delay were within the boundary 328 or was outside the boundary 328 and consequently not permitted. The values of gain, integration window and integration delay selected by the microprocessor 14 for the capture detection circuit 41 must minimally be an allowed or permissible combination. In addition, the autocalibration sequence described below optimizes the tuning of the capture detection circuit 41 by determining the true threshold of massive capture and by determining which parameters allow the earliest possible assessment of capture. Early assessment of capture or determination that capture has not occurred, allows the microprocessor to command the stimulus generator 38 to issue a safety pacing pulse with minimal risk of delivering stimulation during a vulnerable period of the heart.

The memory map is calibrated prior to implantation of the pacemaker, preferably at manufacture. A lead would be attached to the pacemaker and the electrode of the lead placed in a fluid, such as normal saline, in such a manner that an electric circuit is completed through the fluid, that is, either the second electrode of a bipolar electrode pair or the pacemaker can for a unipolar electrode are also electrically connected to the fluid. An initialization program 400 would then be implemented, preferably in the pacemaker, although the program could also be resident in an external programming device. The initialization program 400 would set 402 the gain, integration delay and integration window to a limit of available values, for example, minimum gain, minimum delay and minimum window. The initialization program selects every available combination of values, so the starting point is not critical. In addition other variables for controlling the sensitivity of the evoked potential circuit could be used without departing from the teachings of our invention. The pacemaker delivers 404 a pacing pulse through the test fluid, tests 406 for evoked potential. If potential is not sensed, an "allowed" or "true" state is written into the memory map at the location for the selected settings of gain, integration delay and integration window. If a potential is sensed, the sensitivity of the circuit is too great, and a "not allowed" or "false" state is written into the memory map at the location for the selected sensitivity. One parameter, for example the gain, is then incremented 412. The limit of the gain is then tested 414. If the maximum possible gain is not exceeded, the program returns to apply another pulse at step 404. If the gain has exceeded its maximum limit, the gain is reset 416 to minimum, and the next parameter, for example the integration delay, is incremented 418. The limit of the integration delay is then tested 420. If the maximum possible integration delay is not exceeded, the program returns to apply another pulse at step 404. If the integration delay has exceeded its maximum limit, the integration delay is reset 422 to minimum, and the next parameter, for example the integration window, is incremented 424. The limit of the integration window is then tested 426. If the maximum possible integration window is not exceeded, the program returns to apply another pulse at step 404. If the integration window has exceeded its maximum limit, all possible combinations have been tested and the memory map or truth table is complete.

Figure 16:
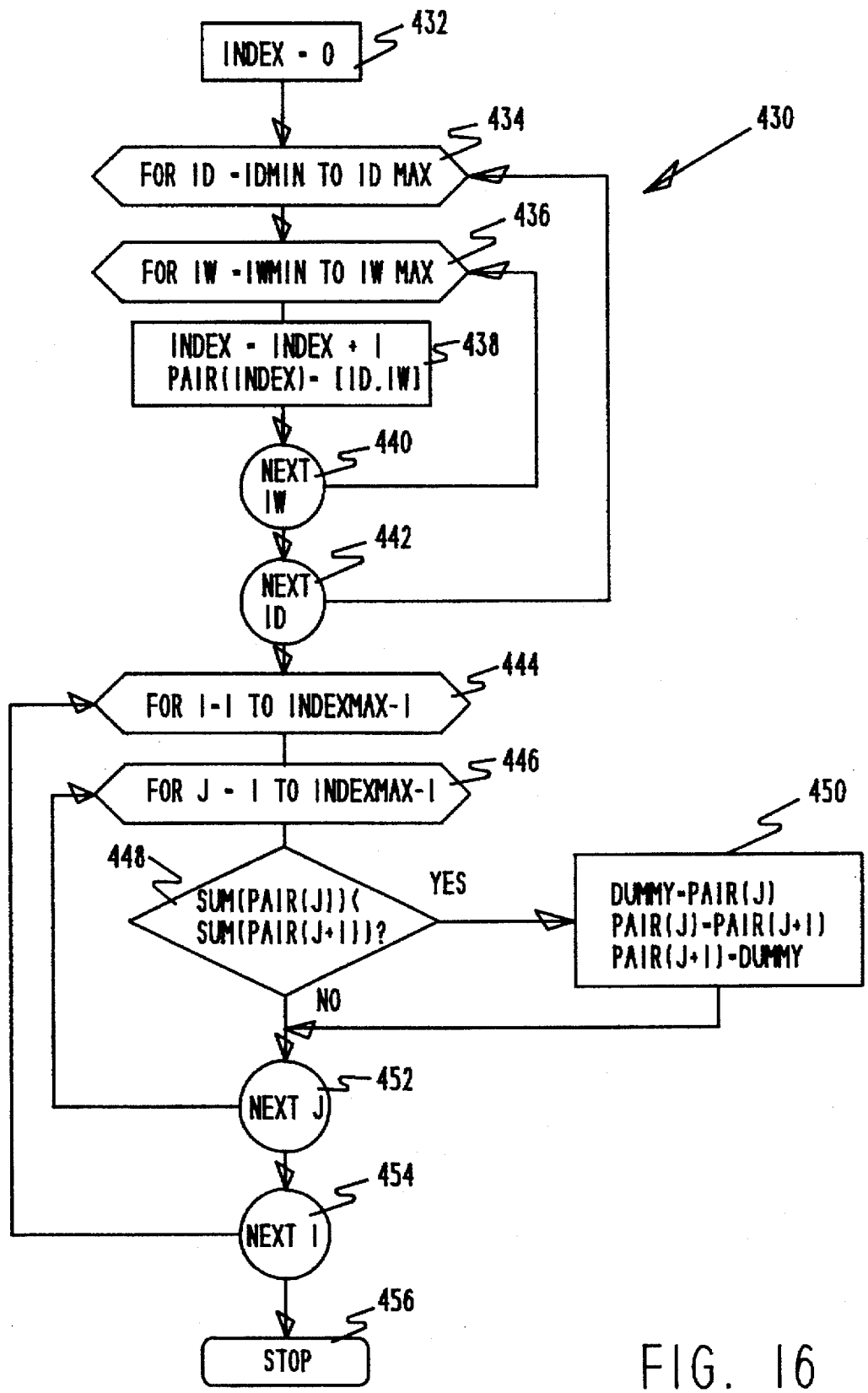
FIG. 16 is a flow chart of a memory map optimization sequence.

It is desirable to recognize the evoked potential within the shortest possible time after a pacing pulse is delivered so that a safety pulse can be administered, if necessary. This means that certain combinations of gain, integration window and integration delay are more desirable than others, specifically, those allowed combinations with the minimum total duration or sum of integration delay and integration window. In addition, minimum gain is preferred, so that local capture is not falsely identified as massive capture. The combinations of integration delay and integration window should be ordered to favor the shortest allowable duration. A suitable program 430 is illustrated in FIG. 16. To produce an ordered sequence or list, the program 430 uses a variable "index" to point to pairs of values for the integration delay and the integration window. A duration for a particular pair is the sum of the integration delay and the integration window. The purpose of the program 430 is to produce an ordered list of pairs such that the duration is consistently increasing or equal. Since the selectable values for the integration delay and the integration window are specific to a particular pacemaker, the program 430 may be implemented in the pacemaker, or in an external programmer, or it may implemented on an independent machine and the resulting list may be used in the pacemaker. The program 430 first generates a complete set of pairs and then orders those pairs by ascending duration.

To produce the set of pairs, the program 430 sets "index", the pointer variable, to zero at step 432. The program executes a function within two nested loops. The first loop, comprised of limits step 434 and increment and return step 442, selects values for the integration delay from the minimum available value to the maximum available value. At each of the integration delay values, the second loop, comprised of limits step 436 and increment and return step 440, selects values for the integration window from the minimum available value to the maximum available value. As each pair of values is selected, a function 438 increments index and assigns the pair of integration delay and integration window at a memory location referenced by index.

To order the pairs by ascending duration, the program 430 executes a sort routine comprised of a test and exchange function within two nested loops. The exterior loop, comprised of limits step 444 and increment and return step 454, increments a counter I from one (1) to the maximum "index" minus one. The interior loop, comprised of limits step 446 and increment and return step 452, increments a counter J from one (1) to the maximum "index" minus one. This provides a sufficient number of passes to completely sort the list of pairs. On each pass, the program tests at 448, comparing the duration, or sum of the integration delay and the integration window, at index equal to J to the duration at index equal to J+1. If duration at J is less than or equal to duration at J+1, then no change in order is necessary. If the duration at J is greater than the duration at J+1, the pairs are exchanged 450, placing the pair at J into location J+1 and the pair at J+1 into location J. When both loops have been completed and the list of pairs has been ordered by ascending duration, the program 430 stops 456.

With the list of ascending duration providing a path and the memory map initialized, the memory map or truth table is ready to be used in the autocalibration sequence of the pacemaker.

Figure 14:
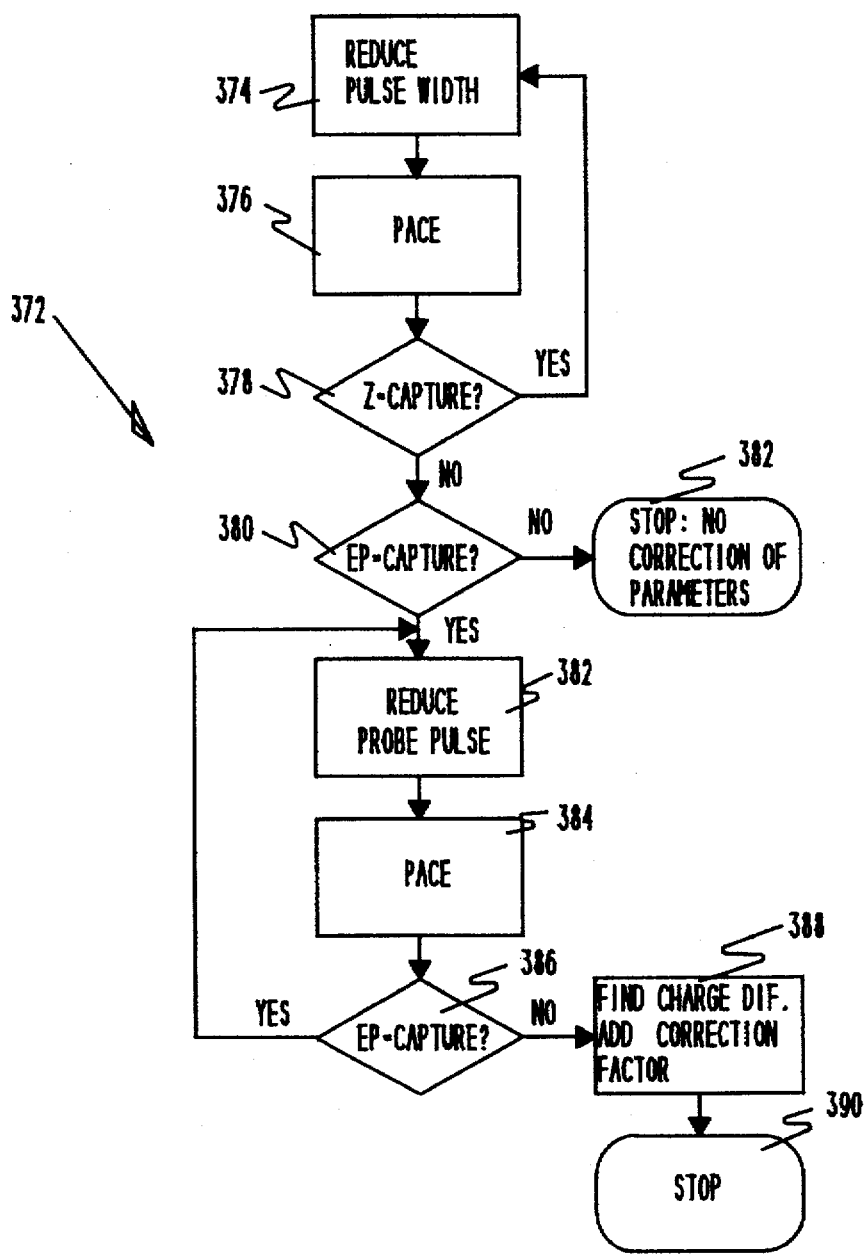
FIG. 14 is a flow chart of a correction factor sequence.
Figure 13:
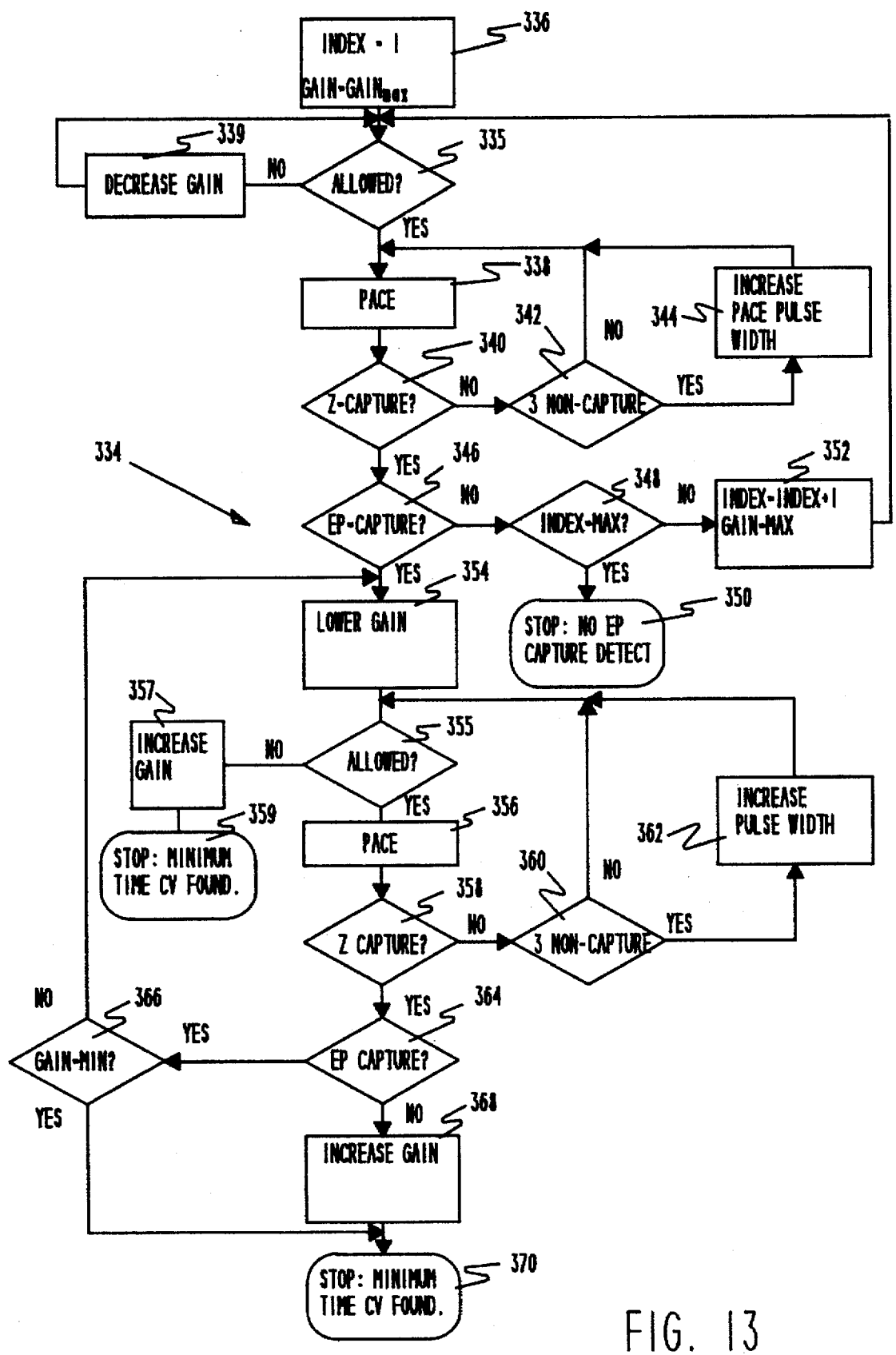
FIG. 13 is a flow chart of an autotuning sequence.
Figure 15:
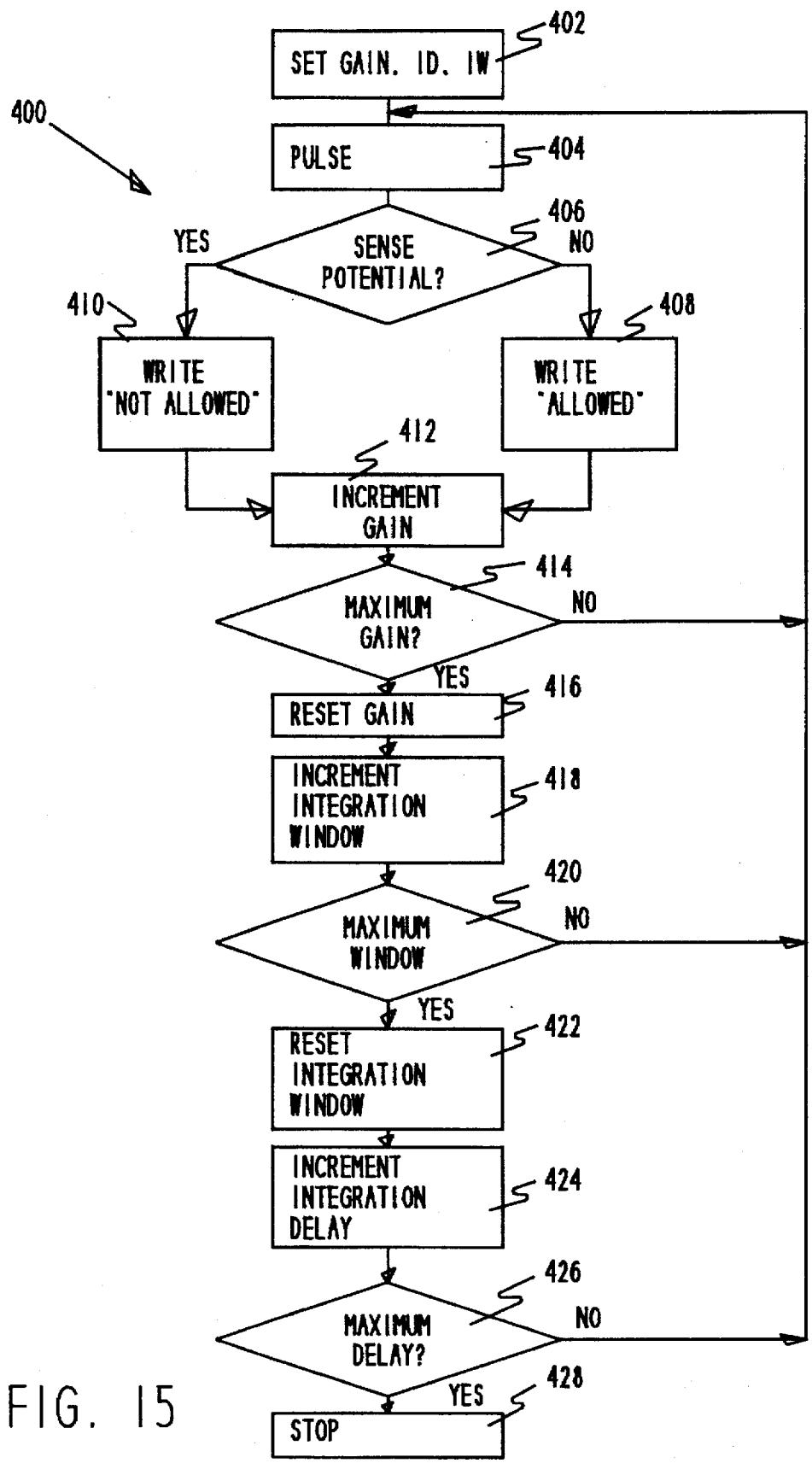
FIG. 15 is a flow chart of a memory map sequence.

Broadly speaking, the autocalibration sequence implemented from time to time in the pacemaker comprises three phases. First, the chronaxie point of the strength duration curve is determined utilizing the impedance based sensor, as described above. Second, at the threshold of capture or only slightly above it, the set of parameters for the evoked potential capture detection circuit 41 are determined which will result in minimal capture assessment time. This step will be further described in connection with the flow chart of FIG. 13. Third, a correction factor representing the additional charge necessary to go beyond localized capture to massive capture is determined. This step will be described in connection with the flow chart of FIG. 14.

As explained above, the autocalibration sequence could be initiated by an external command by a physician using a pacemaker programmer, on a periodic basis as determined by an internal clock in the pacemaker, or upon detection of a selected condition by the pacemaker. Using the impedance, or mechanical response detection circuitry and algorithm, the chronaxie would be determined as described above in connection with FIG. 8. With the pacemaker stimulating pulse now set at capture or slightly above, the microprocessor 14 will initiate the actual tuning of the capture verification circuit 41 with a program sequence 334 illustrated in FIG. 13. In the program sequence 334, the initial parameters of the P1 pulse are set 336 by setting a counter to an initial value, the gain to maximum and index to one, thereby selecting minimum duration for the sum of the integration delay and integration window. The mechanical or impedance dual-pulse procedure is still being applied to avoid loss of capture. The microprocessor checks 335 the memory map to ascertain if the combination of minimum duration and maximum gain is allowed, that is, if the combination does not produce a false indication of capture. If not allowed, the gain is decreased 339, and the test 335 is repeated. After an allowed combination is identified, a pacing pulse 30 is delivered 338. The microprocessor 14 tests 340 the output of the impedance detection circuit 42 for capture. If capture is not detected, the microprocessor 14 will allow 342 a select number, for example 3, additional cycles of pacing stimulation to occur before attempting to adjust the parameters. If capture has not been detected, the pulse width would be increased 344. If capture is detected at 340 by the impedance circuit 42, the microprocessor would test 346 to see if the evoked potential circuit 41 had also detected capture. If capture is not detected, the microprocessor 14 would test 348 to see if the index were maximum, that is, if there were any further increases available in the sensitivity of the evoked potential system. If the index is maximum, indicating that gain integrator delay and integrator width have all been set to their most sensitive available values, the program would indicate 350 that capture verification through the evoked potential circuit 41 is not available. If further increases in sensitivity are permissible, the microprocessor 14 would increment 352 the index, thus selecting the next longer duration (or an equal duration with a different combination of integration delay and integration window), would reset the gain to maximum, and would retry the sequence by returning to the test 335.

Returning now to step 346, if capture is detected by the evoked potential circuit 41, the gain is lowered 354 to the next permissible value, as indicated in the memory map 330. The microprocessor tests 355 the memory map to ascertain if the combination of duration and gain is allowable. If not allowable, the gain is increased 357 and the program 334 stops 359, reporting that minimum duration capture verification has been identified. If the combination is allowed, another pacing pulse pair is applied 356. The microprocessor checks to see if the impedance circuit has detected capture 358. If capture is not detected by the impedance circuit, three additional cycles are permitted by the test 360. If impedance capture is not detected in three cycles, the pulse width or magnitude is increased 362, and this cycle continues until impedance capture is detected. Once impedance capture is detected the microprocessor tests 364 for evoked potential capture as detected by the circuit 41. If capture is detected, the microprocessor 14 will test at 366 to see if the gain is set at the minimum allowable gain for the selected integration delay and integration width. If the gain is not set to minimum, control returns to the lower gain step 354. If it is set to minimum, the program reports that the minimum time for the evoked potential has been found. If capture is not detected at 364, the gain would be increased 368 and the program would again report 370 that the minimum time had been found. The resulting combination of gain integration, delay and integration window would tune the evoked potential circuit 41. The impedance circuit could then be turned off, unless a safety margin is to be determined.

The third and final phase of the auto calibration sequence adds a safety margin to the evoked potential parameters to avoid false positive detection of local capture instead of massive capture. This sequence is illustrated in connection with FIG. 14. Again with both the impedance capture detection circuit and the evoked capture detection circuit operational, the microprocessor 14 would reduce 374 the pulse width of the pacing pulse and pace 376 the select chamber of the heart. The microprocessor 14 would then test for capture 378 by the impedance detection circuit 42. If capture is detected, pulse width would again be reduced incrementally until the impedance circuit 42 no longer reports capture. The microprocessor would then test the evoked potential circuit 41 for capture 380. If capture is not detected no correction of parameters is needed and this program segment would stop 382. If, on the other hand, capture is detected by the evoked potential circuit, this indicates that the circuit is too sensitive and is detecting local capture rather than massive capture. The P1 pulse of the dual pulse impedance capture sequence would again be reduced 382 and the heart paced 384. The microprocessor would test 386 for evoked potential capture. If a false positive is still detected, the P1 pulse would again be reduced 382 and the sequence continued until the evoked potential circuit no longer reports capture. The microprocessor can then calculate the difference between the magnitude of the P1 pulse when capture was lost according to the impedance circuit at step 378 and the value of the P1 pulse when the evoked potential circuit reported loss of capture at step 386. A simple approximation of the difference in charge ΔQ delivered by the two pulses may be calculated as follows:

$$\Delta Q = I_2 \cdot t_2 - I_1 \cdot t_1$$

where I is current equal to V/R and V is the pulse amplitude and R is the impedance measured by the impedance sensor. The duration of a pulse is indicated by t. The subscripts 1 and 2 indicate the pulse when capture was lost according to the evoked potential circuit and according to the impedance circuit, respectively.

A better approximation of the charge difference ΔQ can be obtained using the calculated strength duration curve. From the Lapicque formula for the strength duration curve $$V = a + b/t$$

where a and b are constants for a specific lead configuration. By reason of the calculation of the strength duration curve mentioned above in connection with the determination of the chronaxie, these constants are known. Since $$I = (a+b/t)/R$$

where R is the impedance measured by the impedance sensor, $$Q = (at+b)/R$$

The charge difference ΔQ can be calculated using measured values for t and R derived from the two pulses.

This difference ΔQ represents a measure of possible error in the evoked potential system. A small ΔQ indicates that the evoked potential system will determine capture with acceptable accuracy. Consequently, a stimulating pulse of lower energy can be used, thus conserving battery power and extending the life of the pacemaker. A larger ΔQ indicates that certain restrictions should be placed on setting the magnitude of the stimulating pulse, for example that a larger safety margin must be selected. If ΔQ exceeds a selected, system-dependant limit, reliance on the evoked potential system might not be permitted, and a pre-selected pulse magnitude would be used instead of the smaller, more energy efficient pulse magnitude which use of the evoked potential system allows.

With this correction made, the evoked potential circuit is tuned, and control can be returned to other programming at 390. With the evoked potential circuit 41 tuned, the impedance circuit 42 can be turned off, conserving energy both in the operation of the impedance circuit and its sensing pulses, and the pacemaker return to operation with a single pacing pulse.

Our invention may be embodied in other specific forms without departing from the spirit or essential characteristics thereof. The foregoing description is, therefore, to be viewed in all respects as illustrative and not restrictive. The scope of our invention is defined by the appended claims.

We claim as our invention:

1. A cardiac stimulator, comprising:
   at least one stimulus generator for producing a stimulating pulse, said pulse having an adjustable energy content,
   a sensor circuit for detecting an evoked potential of a heart in response to application of a stimulating pulse, said sensor circuit having an adjustable sensitivity,
   means electrically connected to said sensor circuit and said stimulus generator responsive to said sensor circuit for causing said stimulus generator to produce a safety pulse,
   a sensor for detecting a mechanical action of the heart,
   means for adjusting the sensitivity of said sensor circuit responsive to said mechanical action detecting sensor.

2. The cardiac stimulator according to claim 1 further comprising a control circuit coupled to said generator for causing said generator to generate a sequence of paired stimuli at a selected pacing rate, a leading stimulus of each pair of the paired stimuli having an adjustable energy content beginning with an energy content on one side of a capture threshold, and a trailing stimulus of each pair of the paired stimuli always having an energy content above the capture threshold;
   a circuit for adjusting the energy content of the leading stimulus toward the capture threshold; and
   a circuit coupled to said sensor detecting a substantial change in the mechanical property thereby identifying the capture threshold.

3. The cardiac stimulator according to claim 2, wherein the sensor is an impedance sensor.

4. The cardiac stimulator according to claim 2 further comprising
   a circuit coupled to said controlling circuit adjusting a duration of said first stimulus to an adjusted duration;
   memory circuits coupled to said control circuitry for storing values of said first stimulus whenever a substantial change in said mechanical property is sensed, and
   a microprocessor coupled to said memory circuits for calculating a chronaxie from said capture thresholds and setting a stimulus level as a function of said chronaxie.

5. The cardiac stimulator according to claim 2 wherein said sensor detects said mechanical property of the heart at a calibration time after application of at least one of said stimuli, said calibration time being shorter than said selected time, and further comprising means for eliminating a value of said mechanical property detected at said calibration time from a value of said mechanical property detected at said selected time thereby reducing measurement error.

6. The cardiac stimulator according to claim 1 further comprising means for inhibiting incorrect identification of pulse artifacts as massive capture.

7. The cardiac stimulator according to claim 6 wherein said means for inhibiting comprises a truth table for possible sensitivities of said sensor circuit and means for preventing selection of sensitivities which cause the sensor circuit to identify pulse artifacts as capture.

8. The cardiac stimulator according to claim 7 wherein said sensor circuit further comprises a variable gain amplifier and wherein said means for adjusting said sensitivity controls said variable gain amplifier.

9. The cardiac stimulator according to claim 8 wherein said sensor circuit further comprises an integration circuit and wherein said means for adjusting said sensitivity controls said integration circuit.

10. The cardiac stimulator according to claim 7 wherein said sensor circuit further comprises an integration circuit and wherein said means for adjusting said sensitivity controls said integration circuit.

11. The cardiac stimulator according to claim 1 further comprising means for inhibiting false detection by said sensor circuit of local capture as massive capture.

12. The cardiac stimulator according to claim 11 wherein said means for inhibiting false detection comprises means for determining a difference in charge of said stimulating pulse when loss of capture is detected by said sensor for detecting mechanical action and when loss of capture is detected by said sensor circuit and means for adjusting the sensitivity of said sensor circuit responsive to said difference in charge.

13. A method for adjusting the sensitivity of an electrical evoked response detector in an implantable cardiac stimulator electrically coupled to cardiac tissue, comprising the steps of:

(a) applying a stimulating pulse to at least one chamber of the heart;

(b) detecting the mechanical evoked response;

(c) detecting the electrical evoked response with a sensor circuit;

(d) adjusting the magnitude of the stimulating pulse until loss of capture is detected with respect to said mechanical response; and (e) adjusting the sensitivity of said sensor circuit to detect a corresponding loss of capture.

14. The method according to claim 13 wherein said step of detecting said mechanical evoked response further comprises (b.1) generating a sequence of paired stimuli at a prescribed pacing rate, a leading stimulus of each pair of the paired stimuli having an adjustable energy content beginning with an energy content on one side of the capture threshold, and a trailing stimulus of each pair of the paired stimuli always having an energy content above the capture threshold;

(b.2) applying the sequence of paired stimuli to the cardiac tissues while adjusting the energy content of the leading stimulus toward the capture threshold;

(b.3) detecting a mechanical property of the heart at a selected time after application of at least one of said stimuli; and (b.4) defining the capture threshold to be approximately equal to the energy content of the leading stimulus of the leading stimulus of the paired stimuli that immediately precedes a substantial change in the detected mechanical property.

15. The method according to claim 14, wherein the detected mechanical property is the impedance of the heart.

16. The method according to claim 15 wherein the energy content of the first stimulus is decreased.

17. The method according to claim 16 wherein the voltage of the first stimulus is decreased.

18. The method according to claim 13 further comprising inhibiting incorrect identification of pulse artifacts as massive capture.

19. The method according to claim 18 wherein said step of inhibiting comprises creating a truth table for possible sensitivities of said sensor circuit and preventing selection of sensitivities which cause the sensor circuit to identify pulse artifacts as capture.

20. The method according to claim 19 wherein said step of adjusting said sensitivity comprises a adjusting gain of a variable gain amplifier.

21. The method according to claim 20 wherein said step of adjusting further comprises controlling an integration circuit.

22. The method according to claim 19 wherein said step of adjusting further comprises controlling an integration circuit.

23. The method according to claim 13 further comprising inhibiting false detection by said sensor circuit of local capture as massive capture.

24. The method according to claim 23 wherein said step of inhibiting false detection comprises determining a difference in charge of said stimulating pulse when loss of capture is detected by detecting mechanical action and when loss of capture is detected by electrical evoked response and adjusting the sensitivity of said sensor circuit responsive to said difference in charge.

* * * * *